(12) United States Patent
Borigo et al.

(10) Patent No.: US 9,910,016 B2
(45) Date of Patent: *Mar. 6, 2018

(54) PIEZOELECTRIC SHEAR RINGS FOR OMNIDIRECTIONAL SHEAR HORIZONTAL GUIDED WAVE EXCITATION AND SENSING

(71) Applicant: FBS, Inc., Bellefonte, PA (US)

(72) Inventors: Cody J. Borigo, Port Matilda, PA (US); Steven E. Owens, Bellefonte, PA (US); Joseph L. Rose, State College, PA (US)

(73) Assignee: FBS, INC., Bellefonte, PA (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/878,595

(22) Filed: Oct. 8, 2015

(65) Prior Publication Data

US 2016/0109412 A1 Apr. 21, 2016

Related U.S. Application Data

(60) Provisional application No. 62/064,211, filed on Oct. 15, 2014.

(51) Int. Cl.
*G01N 29/07* (2006.01)
*G01N 29/04* (2006.01)
(Continued)

(52) U.S. Cl.
CPC ......... *G01N 29/043* (2013.01); *G01N 29/069* (2013.01); *G01N 29/07* (2013.01);
(Continued)

(58) Field of Classification Search
CPC .... G01N 29/043; G01N 29/069; G01N 29/07; G01N 29/11; G01N 29/2412;
(Continued)

(56) References Cited

U.S. PATENT DOCUMENTS 3,816,775 A * 6/1974 Khaimov ............... H03H 9/135
310/321
4,072,871 A * 2/1978 Wilson .................. B06B 1/0611
310/333
(Continued)

FOREIGN PATENT DOCUMENTS

JP 05-045346 * 2/1993

*Primary Examiner* — Helen Kwok
(74) *Attorney, Agent, or Firm* — Duane Morris LLP

(57) ABSTRACT

An ultrasonic guided wave system for defect detection in a plate-like structure, includes at least one first circumferentially-polarized piezoelectric $d_{15}$ shear ring element configured to be coupled to a structure. The controller includes a machine readable storage medium and a processor in signal communication with the machine readable storage medium. The processor is configured to cause a pulse generator to pulse the at least first circumferentially-polarized piezoelectric $d_{15}$ shear ring element such that shear horizontal-type guided wave energy is transmitted in all directions in the plate-like structure, process at least one guided wave signal to identify the presence and location of at least one possible defect in the plate-like structure, and store the guided wave signal and defect detection data in the machine readable storage medium.

18 Claims, 26 Drawing Sheets

(51) Int. Cl.
*G01N 29/34* (2006.01)
*G01N 29/06* (2006.01)
*G01N 29/26* (2006.01)

(52) U.S. Cl.
CPC ......... *G01N 29/262* (2013.01); *G01N 29/343* (2013.01); *G01N 2291/0422* (2013.01); *G01N 2291/0425* (2013.01); *G01N 2291/2694* (2013.01)

(58) Field of Classification Search
CPC .. G01N 29/262; G01N 29/343; G01N 29/348; G01N 29/2462; G01N 29/341; G01N 29/221
See application file for complete search history.

(56) References Cited

U.S. PATENT DOCUMENTS

| | | | | |
|---|---|---|---|---|
| 5,473,245 A * | 12/1995 | Silvus, Jr. | ................ | G01B 7/02 310/333 |
| 5,532,541 A * | 7/1996 | Fujishima | .............. | H02N 2/103 310/323.12 |
| 5,629,485 A * | 5/1997 | Rose | ...................... | B64D 15/20 73/170.26 |
| 5,813,998 A * | 9/1998 | Dias | ...................... | G10K 11/24 601/2 |
| 6,396,262 B2 * | 5/2002 | Light | .................. | G01N 17/006 324/220 |
| 7,095,160 B2 * | 8/2006 | Uchino | .................. | H02N 2/166 310/323.03 |
| 7,938,008 B2 * | 5/2011 | Owens | ................. | G01N 29/043 73/599 |
| 8,170,809 B2 * | 5/2012 | Van Velsor | ............ | G01N 29/07 702/39 |
| 8,217,554 B2 * | 7/2012 | Royer, Jr. | ............. | B64D 15/00 244/134 A |
| 9,638,671 B2 * | 5/2017 | Borigo | ................ | G01N 29/069 |
| 2004/0016299 A1 * | 1/2004 | Glascock | ............ | G01N 29/221 73/638 |
| 2006/0190080 A1 * | 8/2006 | Danoff | ................ | A61F 2/30721 623/17.11 |
| 2010/0217544 A1 * | 8/2010 | Yan | ........................ | G01N 29/07 702/56 |
| 2012/0279308 A1 * | 11/2012 | Yan | ....................... | G01N 29/045 73/636 |
| 2013/0327148 A1 * | 12/2013 | Yan | ........................ | G01N 29/34 73/628 |
| 2014/0125199 A1 * | 5/2014 | Furuta | ................ | C04B 35/4682 310/323.06 |
| 2015/0053009 A1 * | 2/2015 | Yan | ........................ | G01N 29/07 73/598 |

* cited by examiner

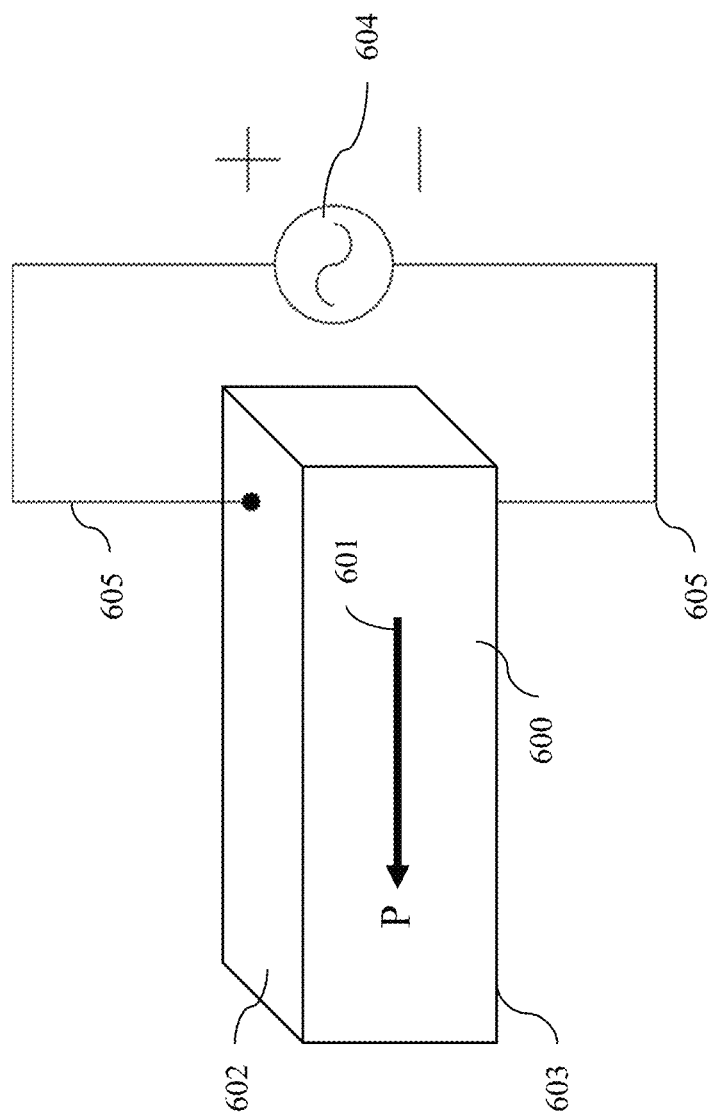

607

606

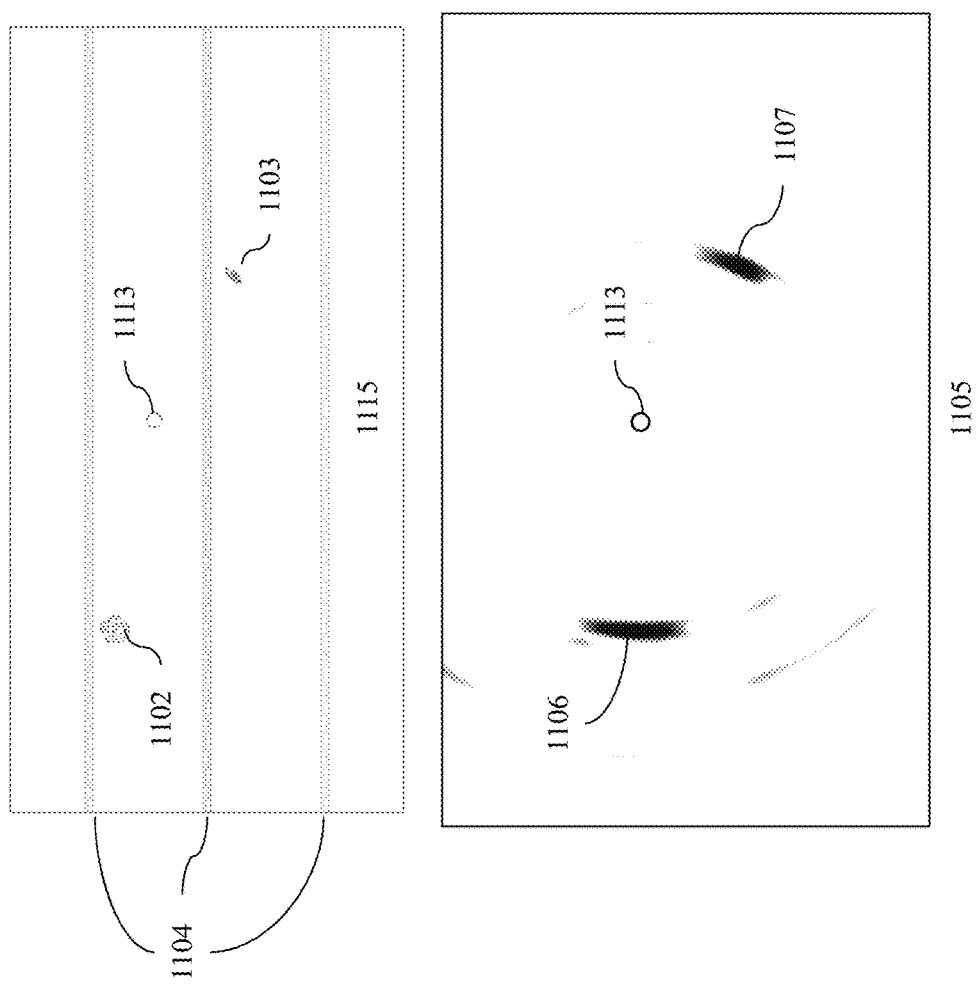

US 9,910,016 B2

PIEZOELECTRIC SHEAR RINGS FOR OMNIDIRECTIONAL SHEAR HORIZONTAL GUIDED WAVE EXCITATION AND SENSING

CROSS-REFERENCE TO RELATED APPLICATIONS

This application claims priority to U.S. Provisional Patent Application No. 62/064,211, filed Oct. 15, 2014, the entirety of which is incorporated by reference herein.

FIELD OF DISCLOSURE

The disclosed systems and methods relate to the non-destructive inspection and structural health monitoring. More specifically, the disclosed systems and methods relate to non-destructive inspection and structural health monitoring of plate-like structures using shear horizontal-type guided waves.

BACKGROUND

Various systems and methods exist for structural heath monitoring ("SHM") and/or non-destructive examination ("NDE") of plates and plate-like structures such as those used on pressure vessels, aircraft fuselages and wings, ship hulls and storage tanks to identify only several possible uses. However, these systems and monitoring/examination techniques are mostly based on point-to-point inspections and are not capable of performing rapid large area monitoring and/or inspection. Guided wave inspection of such structures is also employed, wherein at one or more guided wave modes are transmitted and received in said structures to carry out the NDE and/or SHM. However, such guided wave techniques using shear horizontal-type guided wave modes with piezoelectric transducers are often limited by the directionality of $d_{15}$ shear bar elements.

SUMMARY

An ultrasonic guided wave system for defect detection in a plate-like structure, includes at least one first circumferentially-polarized piezoelectric $d_{15}$ shear ring element configured to be coupled to a structure. The controller includes a machine readable storage medium and a processor in signal communication with the machine readable storage medium. The processor is configured to cause a pulse generator to pulse the at least one first circumferentially-polarized piezoelectric $d_{15}$ shear ring element such that shear horizontal-type guided wave energy is transmitted in all directions in the plate-like structure, process at least one guided wave signal to identify the presence and location of at least one possible defect in the plate-like structure, and store the guided wave signal and defect detection data in the machine readable storage medium.

BRIEF DESCRIPTION OF THE DRAWINGS

FIG. 6A illustrates a piezoelectric $d_{15}$ shear bar element.

FIG. 11C illustrates one example of SH guided wave phased array results generated on a steel plate-like structure using a 16-element shear ring phased array.

DETAILED DESCRIPTION

Figure 1:
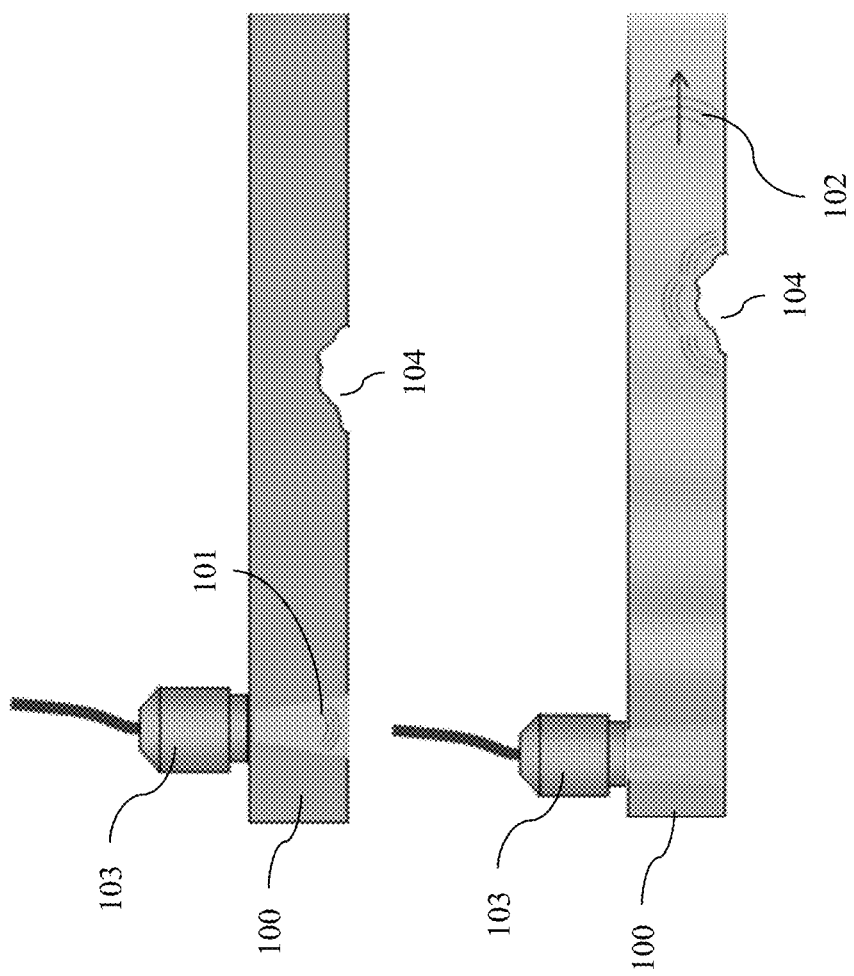
FIG. 1 illustrates the concept of guided waves in a plate-like structure and compares them to bulk waves.

This description of the exemplary embodiments is intended to be read in connection with the accompanying drawings, which are to be considered part of the entire written description.

Circumferentially-polarized piezoelectric $d_{15}$ shear ring elements are utilized to generate and detect shear horizontal-type guided waves in plate-like structures to perform at least one of non-destructive evaluation and structural health monitoring of said plate-like structures. The omnidirectional SH-wave generation and sensitivity characteristics of said elements yields superior guided wave results in many embodiments when compared to highly-directional piezoelectric $d_{15}$ shear bar elements.

In some embodiments, at least one shear ring element is coupled to a structure to generate SH guided waves in all directions in said structure. The at least one ring element may also be coupled to the structure to detect SH guided waves impinging on the element location from any direction. These waves may have been generated by the at least one ring element or by another element or energy source such as an impact or crack growth and may also be reflections from a defect.

In some embodiments, a plurality of shear ring elements are coupled to a structure in an array around a perimeter of an area to be monitored using guided wave CT imaging. SH wave signals are transmitted between all shear ring elements in the array and a damage probability function, which accounts for both direct and indirect wave paths, is mapped onto each signal path and scaled according to at least one signal parameters to generate a pseudo-image of damage in the structure within the array perimeter. In some embodiments, baseline data is used as a reference comparison for the guided wave signals.

In some embodiments, at least two shear ring elements are coupled to a structure, and at least one of time delays and amplitude factors are applied to the individual elements to generate SH guided waves in the structure that are focused to at least one point or steered in at least one direction in said structure. Reflections from defects or structural features are then detected by the at least two shear ring elements and recorded in a machine readable medium. The recorded guided wave data is subsequently processed to determine the presence, location, and severity of defects in the structure and generate a pseudo-image of the structure. Back-propagation post-processing is also applied to the collected guided wave data in some embodiments to further improve focusing and beam steering capabilities.

In some embodiments, at least two shear ring elements are coupled to a structure in a concentric configuration to form an annular array transducer that is capable of preferential guided wave mode selection based on the spacing and width of the elements. The annular array element width and spacing is based on a zero-order Bessel function. Amplitude factors and time delays are applied to the individual shear ring elements that comprise the phased array.

Guided waves are formed from the constructive interference of ultrasonic bulk waves that have interacted with the boundaries of the structure in which they propagate. A conceptual illustration of this concept is provided in FIG. 1, in which bulk waves 101 and guided waves 102 are shown being generated in an identical plate-like structure 100 using ultrasonic transducers 103. Guided waves are unique in the sense that they are capable of propagating for long distances compared to traditional ultrasonic waves and can be used to inspect hidden/inaccessible structures like buried or cased piping, plates behind walls or insulation, etc., which allows them to detect corrosion 104 or other defects from remote locations. Unlike "spot-checking" with traditional ultrasonic techniques, guided waves are able to provide up to 100% volumetric inspection. Furthermore, guided waves provide an efficient and cost-effective means of inspection due to increased inspection speed and simplicity, particularly for large structures that would require a large number of ultrasonic bulk wave spot-check measurements as described in Rose, J. L., *Ultrasonic Guided Waves in Solid Media*, Cambridge University Press, New York, N.Y., 2014, the entirety of which is incorporated by reference herein.

Figure 2:
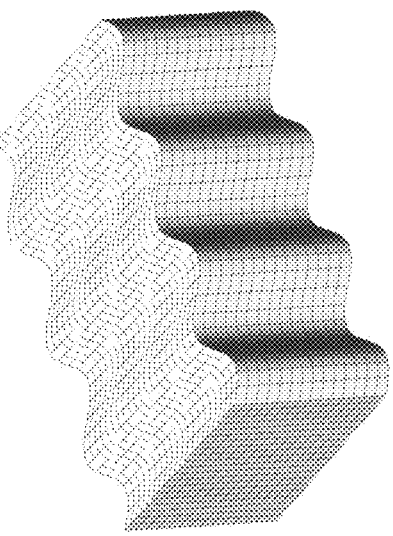
FIG. 2 illustrates the vibration of Lamb-type and SH-type guided waves in a structure.
Figure 2:
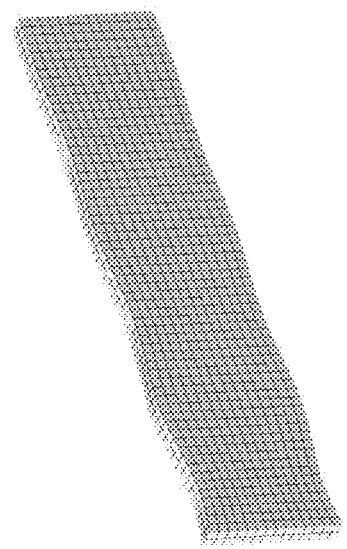
Figure 2:
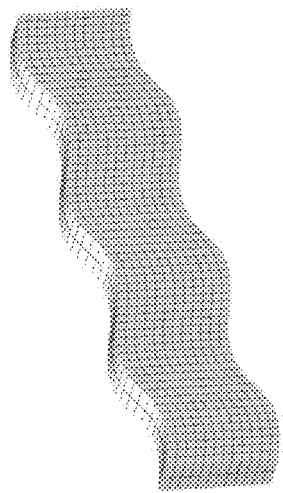

In plates and plate-like structures, i.e. structures whose radius of curvature is much greater than their thickness, there are two primary types of guided wave modes that can be excited: Lamb and shear horizontal (SH). The general propagation characteristics of these two mode types are illustrated in FIG. 2, wherein a cross-sectional view of a solid plate under deformation induced by an $A_0$ Lamb wave 200, an $S_0$ Lamb wave 201, and an SH wave 202 are illustrated. In some embodiments, SH-type waves, which have the defining characteristic of generating only in-plane lateral vibration as they propagate through a structure, are used. On the other hand, Lamb-type waves generate out-of-plane vibration and in-plane vibration parallel to the wave propagation direction as described in Rose, J. L., *Ultrasonic Guided Waves in Solid Media*, Cambridge University Press, New York, N.Y., 2014, the entirety of which is incorporated by reference herein.

Figure 3:
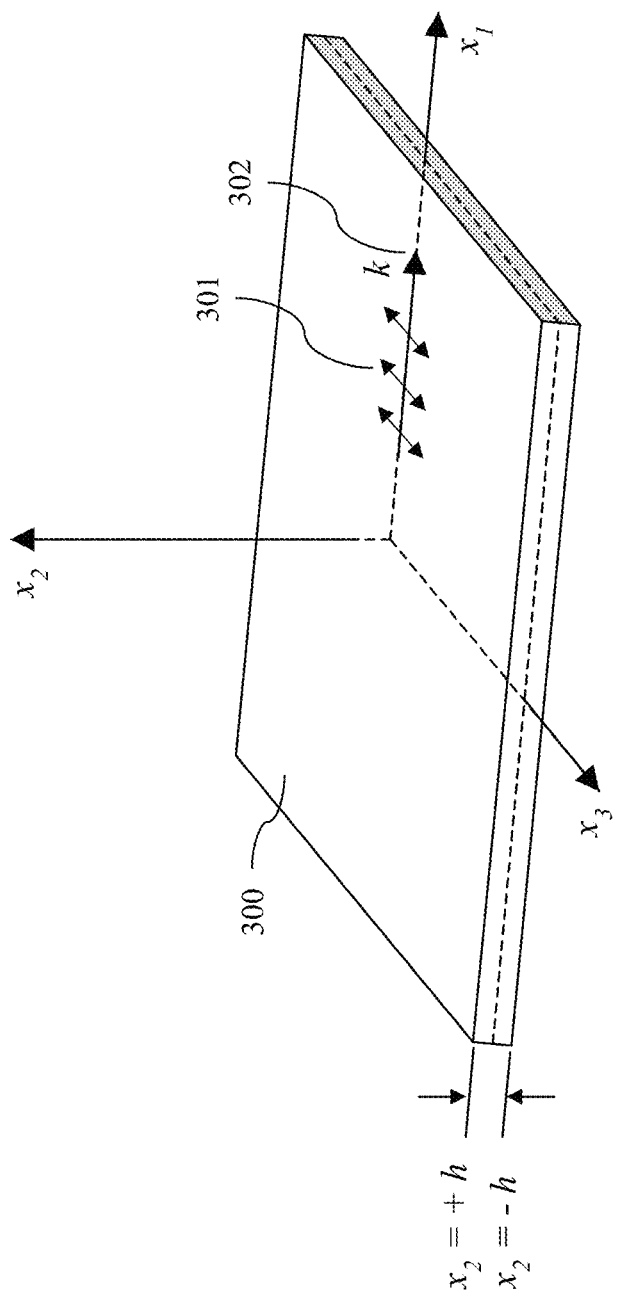
FIG. 3 illustrates the vibration components and propagation direction of SH-type guided waves in a structure.

FIG. 3 illustrates the concept of SH-type waves having in-plane lateral vibration 301 that are perpendicular to the wave propagation direction 302 in a plate 300. The terms "Lamb wave" and "SH wave" can be strictly defined as these types of guided waves in homogenous, linear, isotropic plates having constant thickness. However, for the purposes of this disclosure, the terms "Lamb wave" and "SH wave" will be more broadly used to describe any of the Lamb-type and SH-type waves in plate-like structures that closely match the characteristics of the waves described by these strict definitions, including plates with a small degree of curvature and anisotropic plates.

Figure 4:
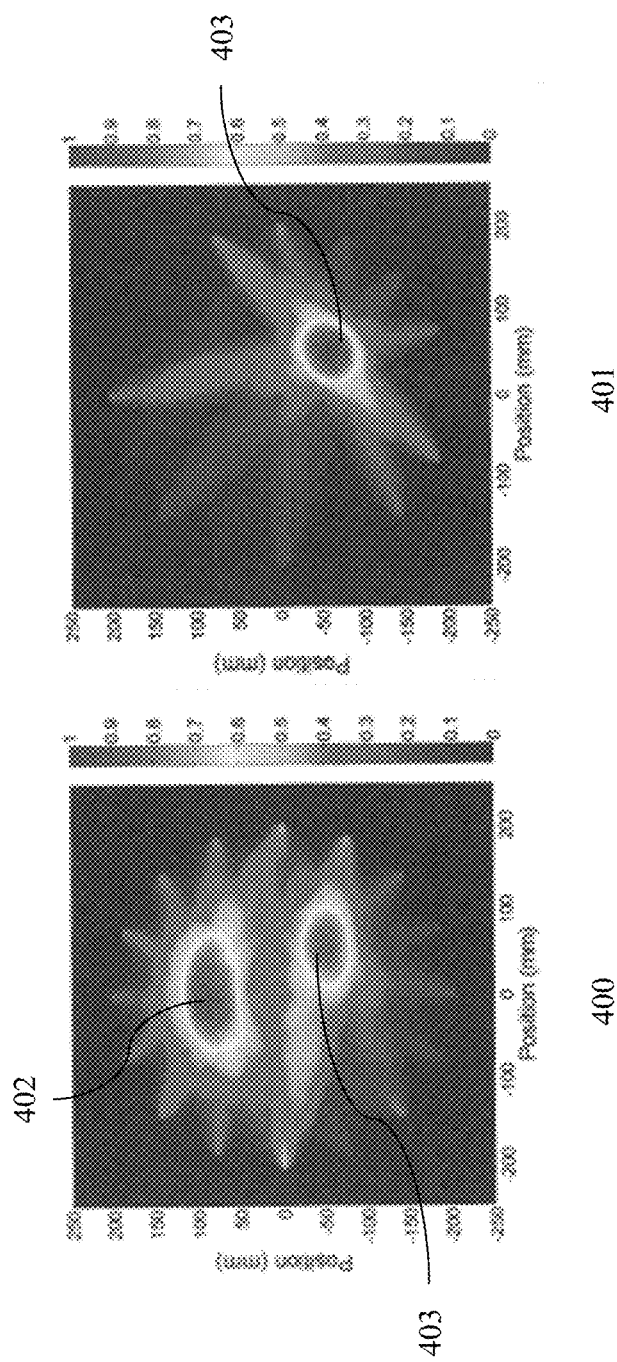
FIG. 4 illustrates guided wave CT images generated with a fluid-sensitive guided wave mode and a fluid-insensitive guided wave mode.

The unique pure shear characteristic of SH waves makes them particularly useful for many non-destructive evaluation (NDE) and structural health monitoring (SHM) applications. For instance, SH waves are insensitive to the presence of inviscid liquids, which means that they are not attenuated by fluid-loaded boundary conditions of a structure such as a fluid-filled pipe, a ship hull with fluid on one side, or a submerged plate. Additionally, this insensitivity to fluids also means that SH wave measurements collected on a structure with and without fluid loading are practically identical, which is useful for the purposes of SHM wherein guided wave signals are compared over time and sensitivity to environmental conditions like rain or fluid-loading are undesirable. One example of the advantage to insensitivity to fluids is shown in FIG. 4, wherein a first computed tomogram (CT) image 400 was generated using a guided wave mode that is sensitive to fluid loading and a second CT image 401 was generated using guided wave modes that are insensitive to fluid loading. The guided wave system used to generate image 400 was unable to distinguish the corrosion defect 403 and the surface liquid 402, while the system designed to utilize fluid-insensitive guided wave modes only detects the corrosion defect 403.

Figure 5:
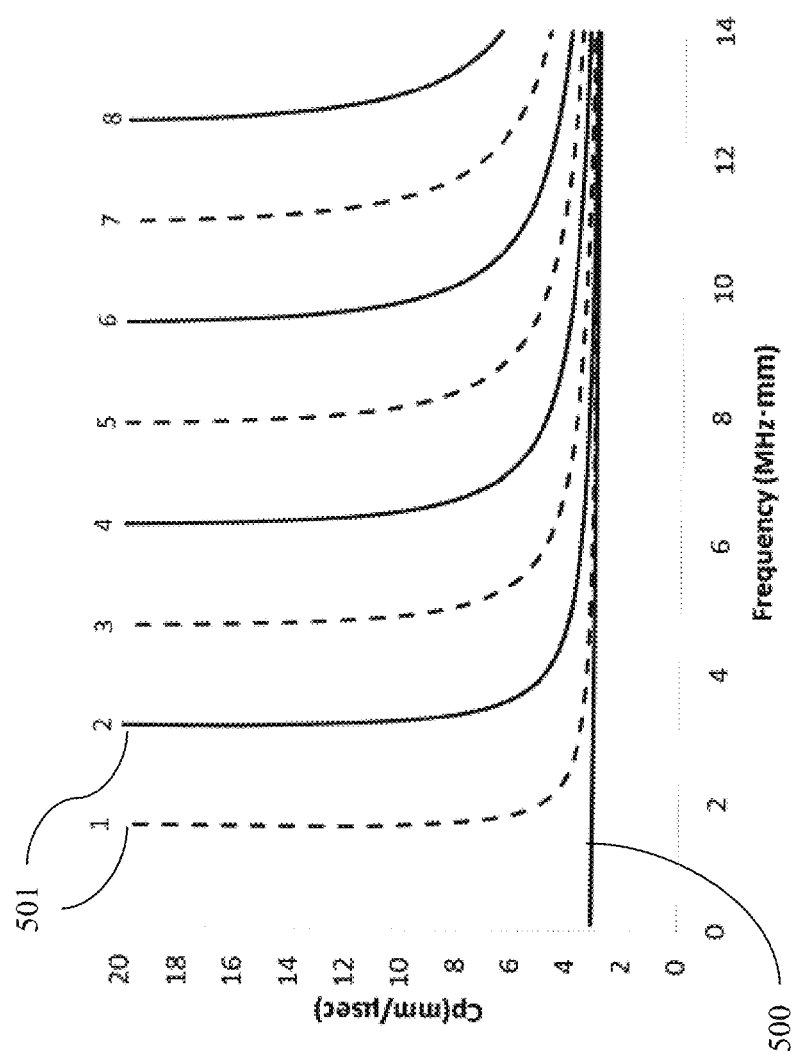
FIG. 5 illustrates the dispersion curves for SH wave modes in an isotropic plate-like structure.

SH waves also have the advantage of generally having simpler propagation characteristics than Lamb waves, particularly with respect to their velocity characteristics and the reduced number of higher order modes. Dispersion curves for SH wave modes in an isotropic plate are provided as one example in FIG. 5. Here it is apparent that the fundamental $SH_0$ mode 500 is strictly non-dispersive, i.e., the velocity is independent of frequency, which can be highly advantageous for NDE and SHM due to the simplicity of processing the guided wave data collected with such a mode. There are also fewer higher-order guided wave modes 501 at any given frequency than for Lamb waves in a comparable structure, which can make signal interpretation and system design simpler.

Figure 6B:
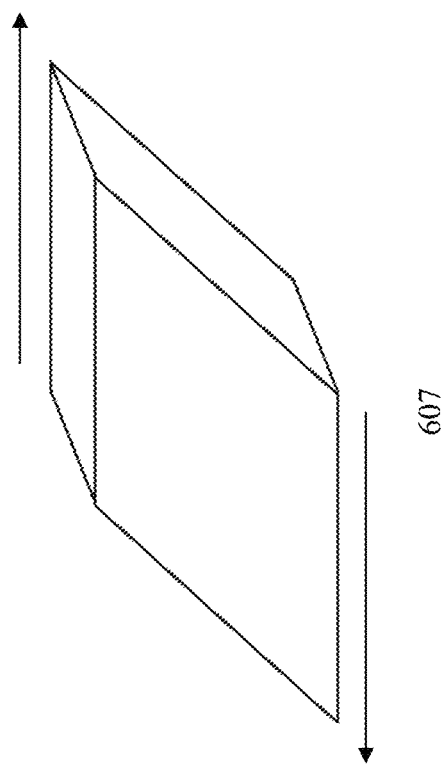
FIG. 6B illustrates the deformation mode of a piezoelectric $d_{15}$ shear bar element.
Figure 6B:
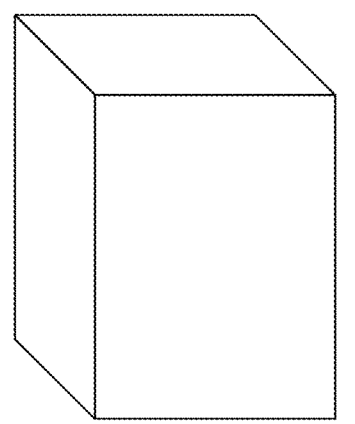

Piezoelectric transducers are often used to generate and to detect guided waves for the purposes of NDE and SHM. To generate SH waves in a structure, the $d_{15}$ piezoelectric coefficient is typically employed in shear block element transducers such as the one illustrated in FIG. 6A. Here the piezoceramic element 600 is polarized in the direction indicated by the arrow 601 and an electric potential is applied across the electrode faces 602 and 603 using the alternating voltage source 604 attached with leads 605. As illustrated in FIG. 6B, when the voltage is applied to the undeformed shear $d_{15}$ piezoelectric element 606, it shears into a deformed state 607. When the base of such an element is coupled to a structure using a rigid bond or viscous couplant, these shear vibrations are transmitted to the structure and SH guided waves can be generated. Conversely, impinging SH waves can also be detected by said transducers by in inverse effect.

Figure 7A:
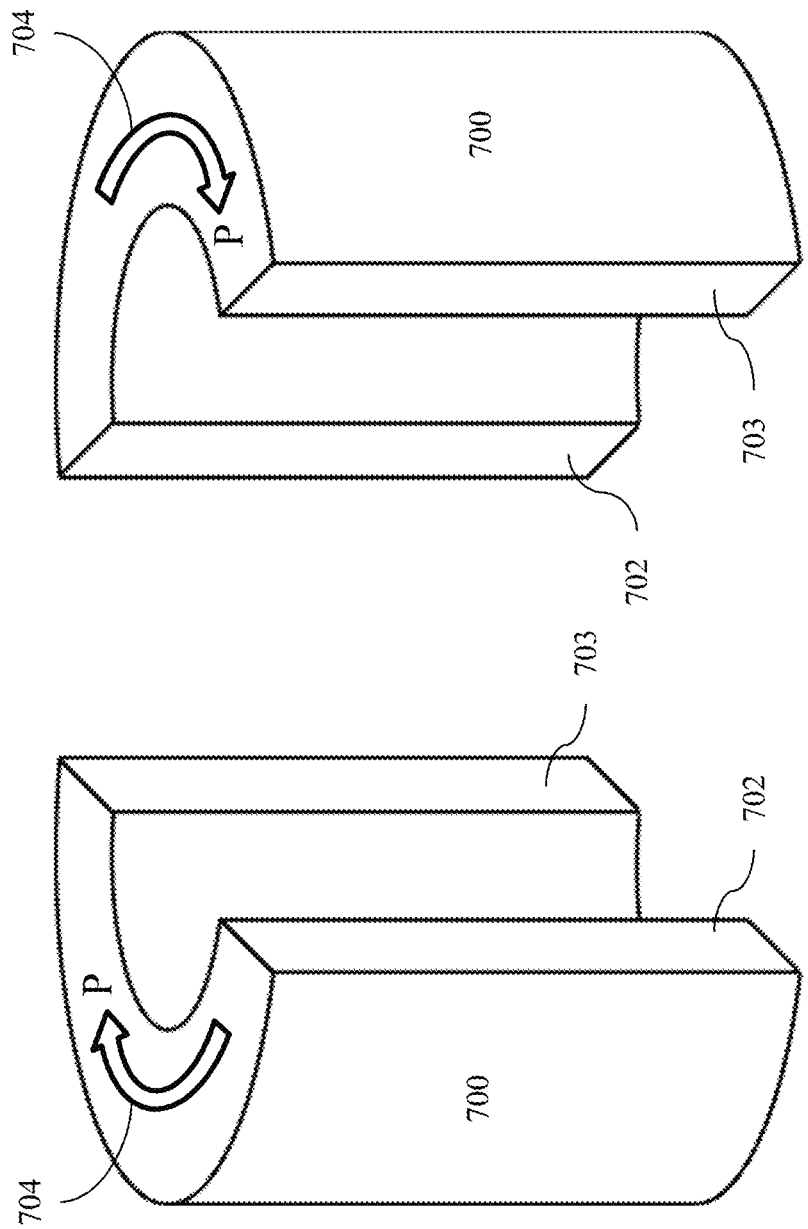
FIG. 7A illustrates the poling and assembly process of a circumferentially-poled piezoelectric $d_{15}$ shear ring element.
Figure 7B:
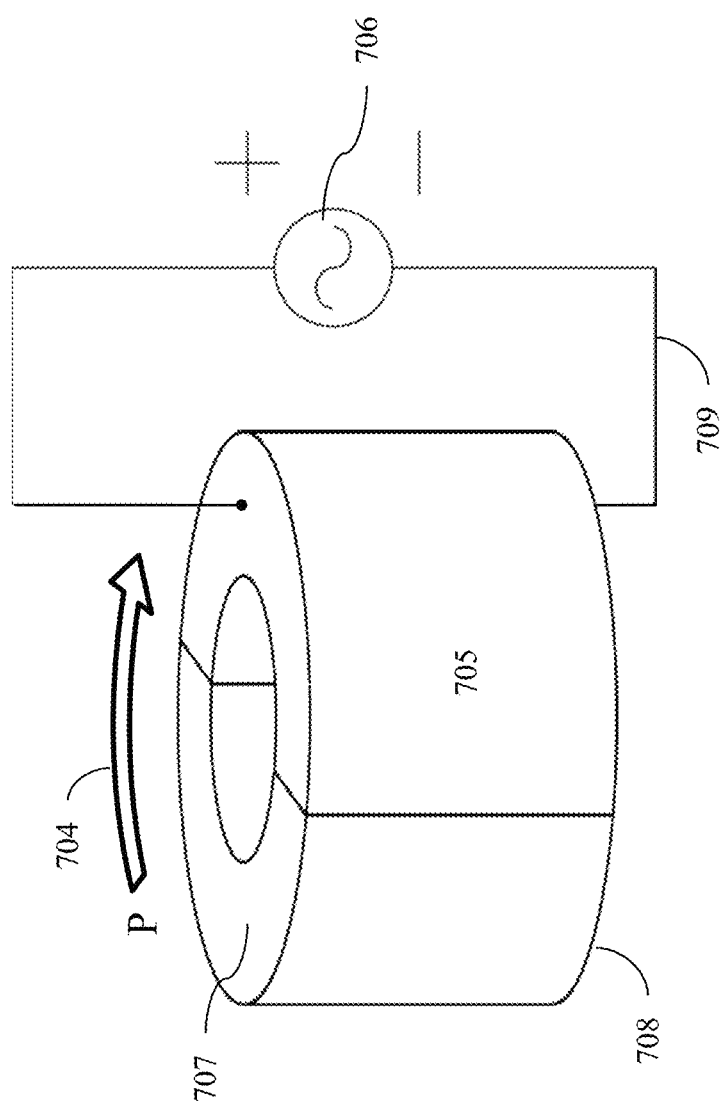
FIG. 7B illustrates a circumferentially-poled piezoelectric $d_{15}$ shear ring element.
Figure 7C:
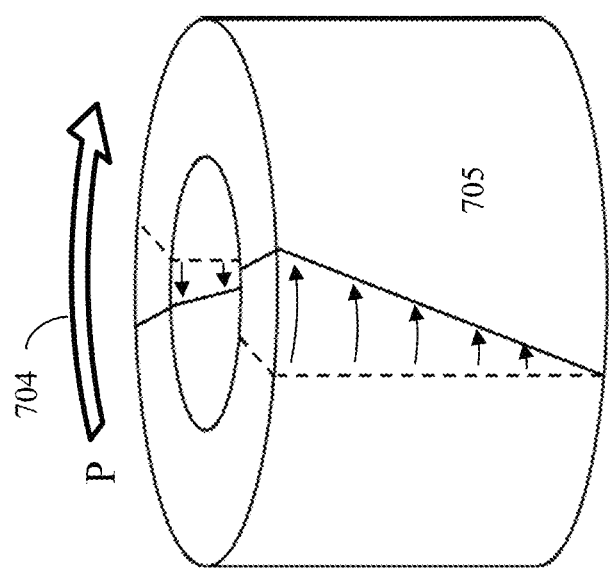
FIG. 7C illustrates the deformation mode of a circumferentially-poled piezoelectric $d_{15}$ shear ring element.

Another type of shear piezoelectric element is the circumferentially-polarized $d_{15}$ shear piezoelectric ring element that was developed by APC International, Ltd. of Mill Hall, Pa., USA and is illustrated in FIGS. 7A and 7B. The shear ring element is fabricated from two half rings 700 that are polarized quasi-circumferentially, in accordance with arrows 704, by applying high-voltage DC poling electrodes to the two vertical faces 702 and 703 (FIG. 7A) while the temperature of the element is greater than the Curie temperature. These half rings 700 are subsequently bonded together to form a full ring element 705, which can be excited with voltage source 706 applied to the upper and lower electrode surfaces 707 and 708 via leads 709 as shown in FIG. 7B. The torsional vibration mode of the shear ring element is illustrated in FIG. 7C. This torsional deformation effectively excites SH guided waves omnidirectionally when coupled to a plate-like structure. The inner and outer radii, the thickness, and the piezoceramic material selected for the rings can all be adjusted to suit the specific requirements of the application as will be understood by people of ordinary skill in the art. Additional variations upon this transducer design also are possible, and the specific embodiment detailed herein is non-limiting and used as one example of an omnidirectional piezoelectric $d_{15}$ shear ring element for SH-type guided wave generation in accordance with some embodiments. Additional embodiments may include shear rings that are fabricated from more than two segments, shear rings that are poled through the radius instead of the thickness dimension, and shear rings that are polygonal instead of truly circular.

Figure 8A:
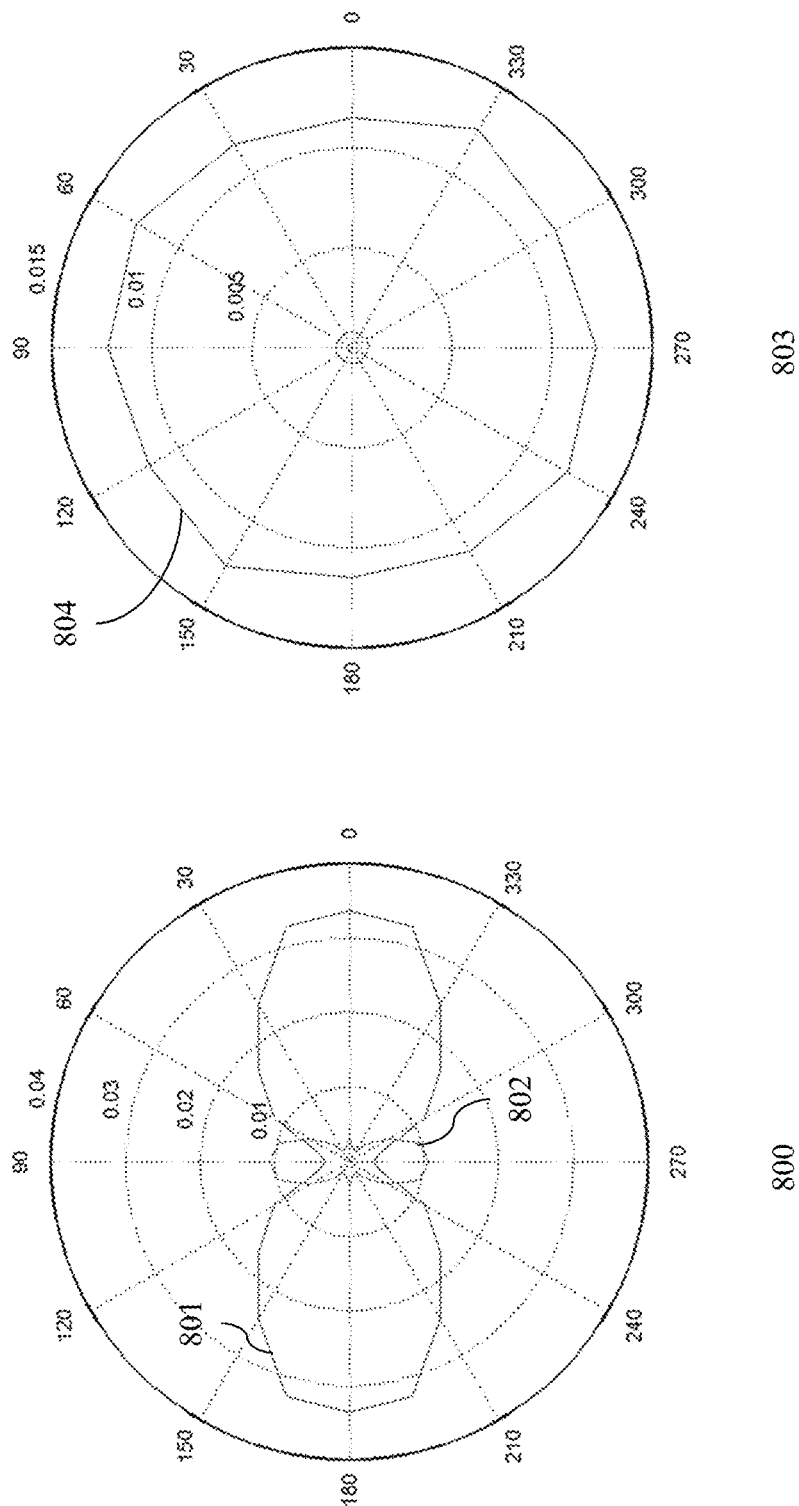
FIG. 8A illustrates the guided wave mode directionality of a piezoelectric $d_{15}$ shear bar element and a circumferentially-poled piezoelectric $d_{15}$ shear ring element.
Figure 8B:
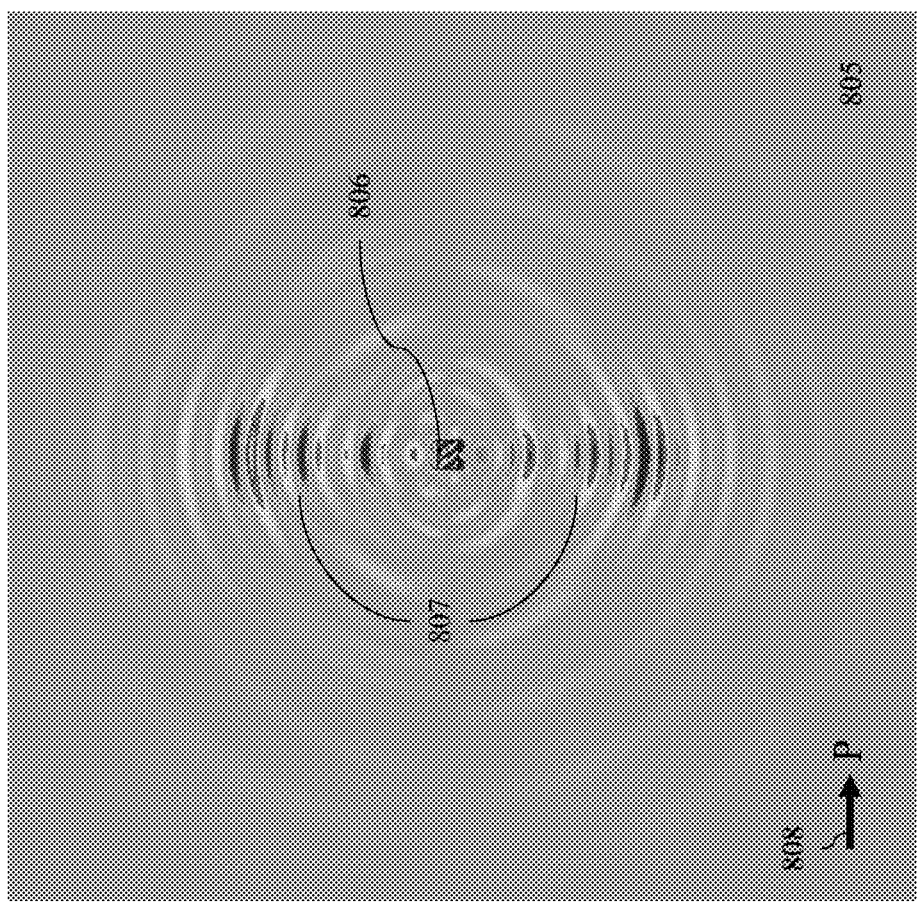
FIG. 8B illustrates the stress field output from a finite element model of a piezoelectric $d_{15}$ shear bar element.

Shear $d_{15}$ piezoceramic elements are highly directional in terms of SH wave excitation and sensitivity. This is illustrated by the experimental results provided in FIG. 8A, wherein the amplitude of the $SH_0$ and $S_0$ guided wave modes were recorded as a function of angle relative to a small $d_{15}$ piezoelectric shear bar and a circumferentially-polarized $d_{15}$ shear ring in polar plots 800 and 803, respectively. In the polar plot 800 corresponding to the shear bar element, it is apparent that the $SH_0$ amplitude 801 is maximized at 0° and 180° and nearly zero at 90° and 270°. The $S_0$ wave amplitude 802 generated by these bars is maximized at 90° and 270° and nearly zero at 0° and 180°. This high degree of directionality is undesirable in many cases. Alternatively, the polar plot 803 corresponding to the shear ring element shows that the $SH_0$ amplitude 804 is equivalent in all directions, which can be a highly advantageous in many cases. The directionality of the $d_{15}$ shear bar elements is also illustrated in FIG. 8B, which is a shear stress field output from a finite element model of a plate 805 induced by shear bar element 806, which is polarized in the direction indicated by 808. The high degree of directionality is apparent by the beams of $SH_0$ guided wave energy 807 emitted by the element. In this respect, the shear ring element is far superior to the shear bar element for many guided wave applications.

Figure 9A:
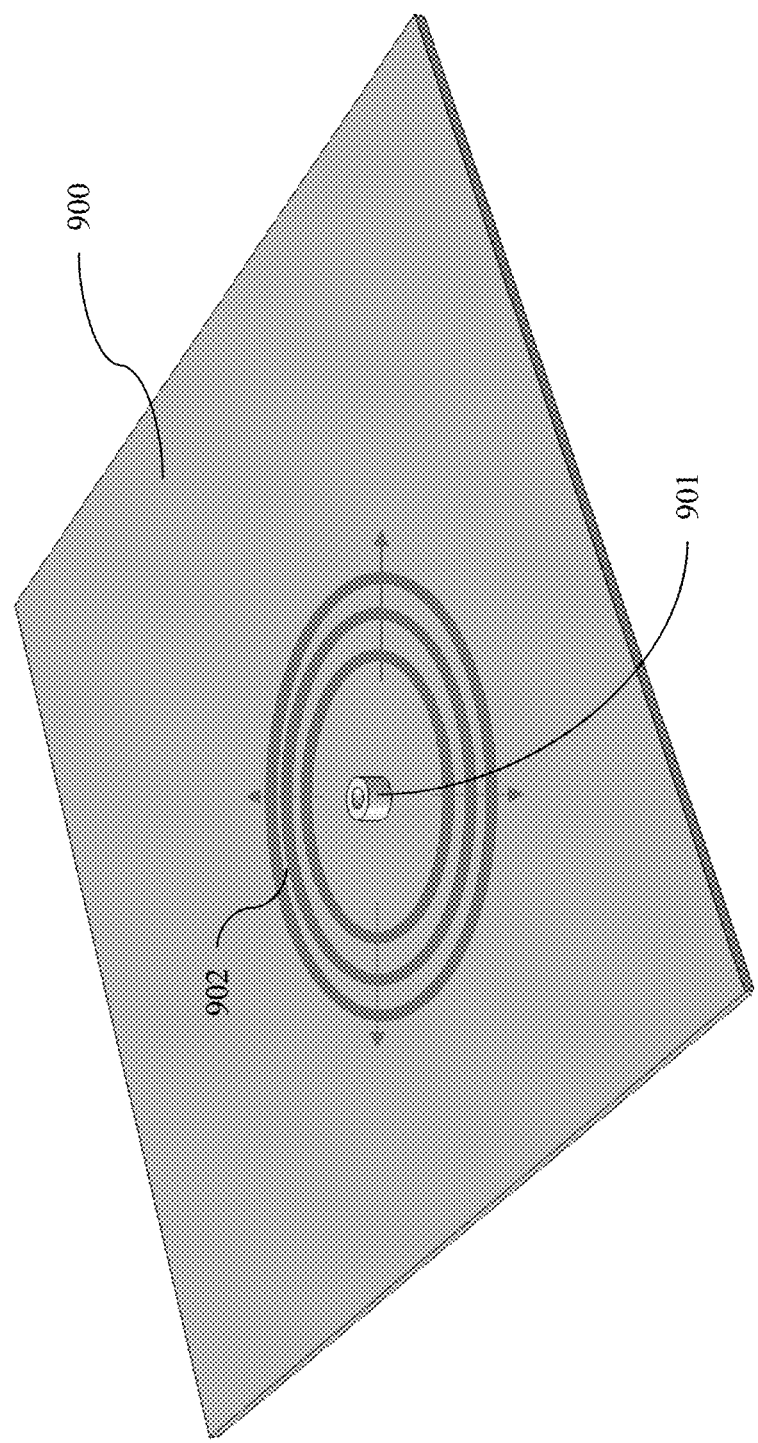
FIG. 9A illustrates a shear ring element coupled to and generating SH guided waves in a plate-like structure.
Figure 9B:
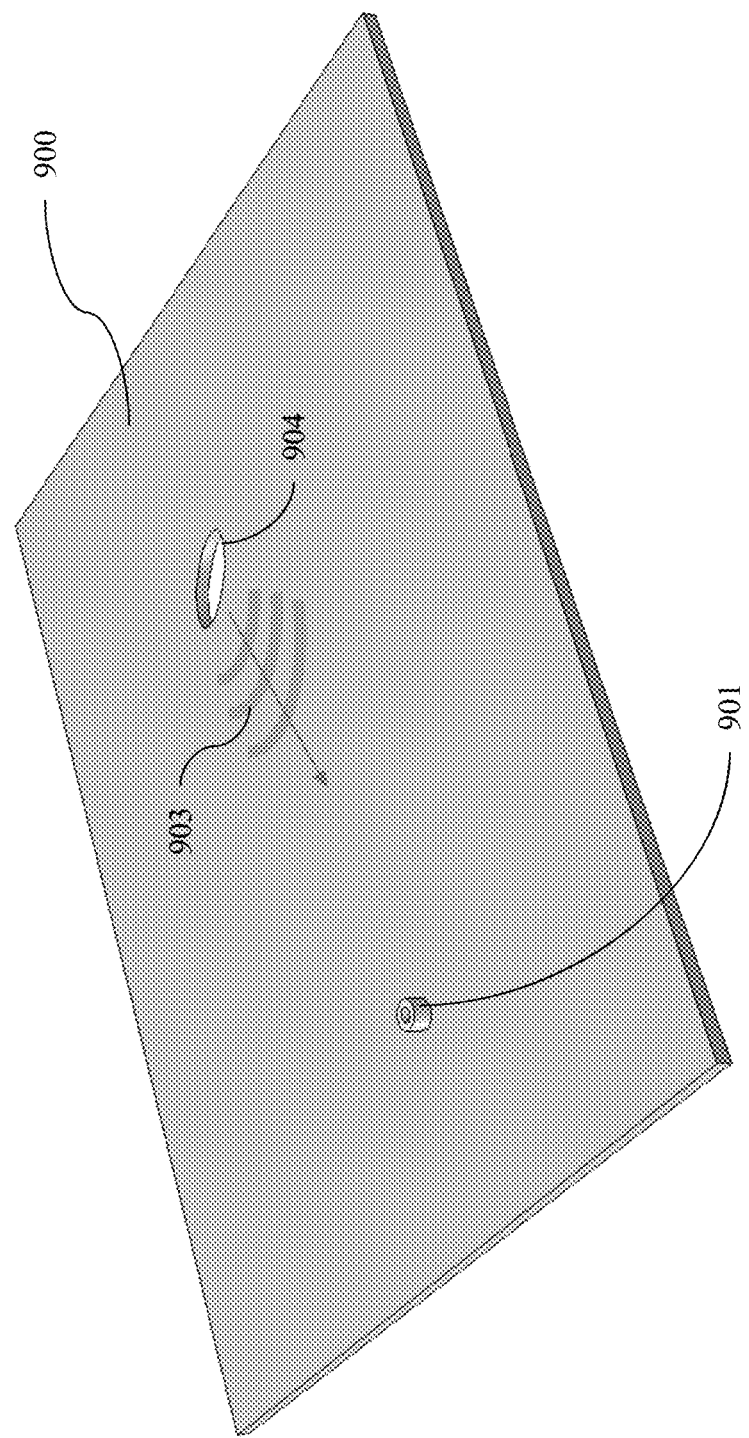
FIG. 9B illustrates a shear ring element coupled to and detecting SH guided waves in a plate-like structure.
Figure 9C:
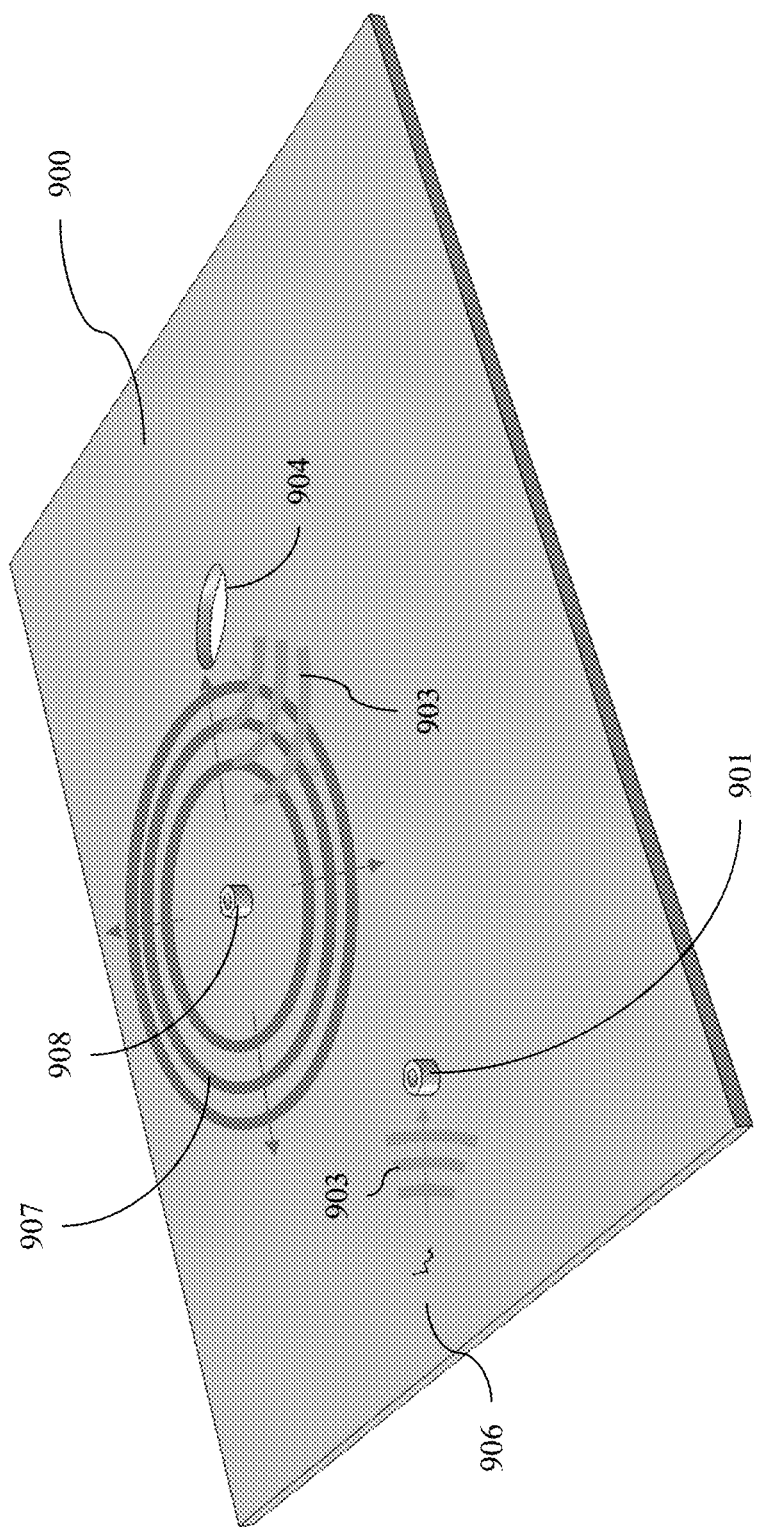
FIG. 9C illustrates two shear ring elements coupled to and generating and detecting SH guided waves that are interacting with various defects in a plate-like structure.

FIGS. 9A-9C illustrate some embodiments, wherein at least one shear ring element 901 is coupled to a structure 900 to generate SH guided waves 902 in all directions in the structure. The at least one ring element 901 may also be coupled to the structure to detect SH guided waves 903 impinging on the element location from any direction as shown in FIG. 9B. As shown in FIG. 9C, waves 907 and 903 may have been generated by said element 901 or by another element 908 or energy source such as an impact or crack growth 906 and may also be reflections 903 from a defect such as a crack 906, a delamination, corrosion, or a hole 904.

Figure 10A:
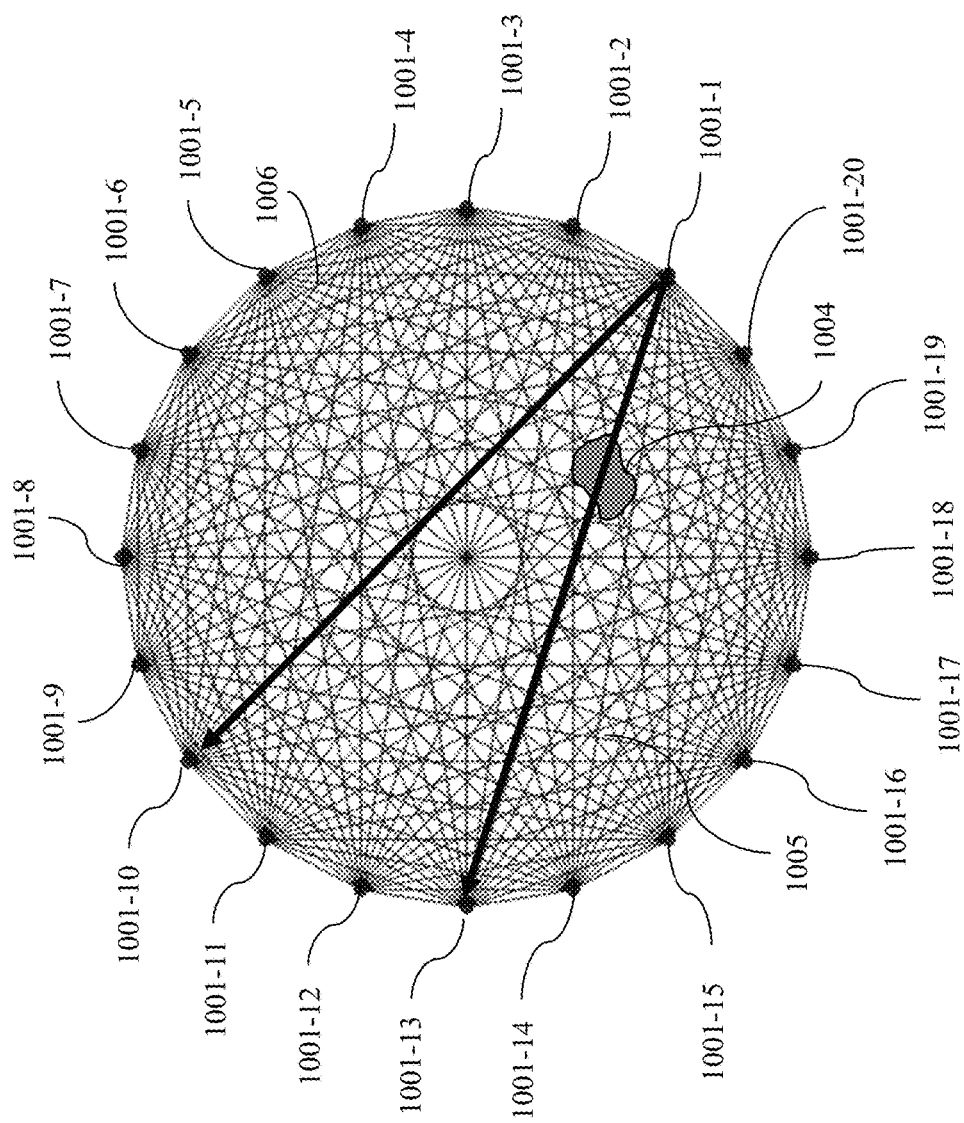
FIG. 10A illustrates an array of shear ring sensors around the perimeter of an area to be monitored with guided wave CT imaging.
Figure 10B:
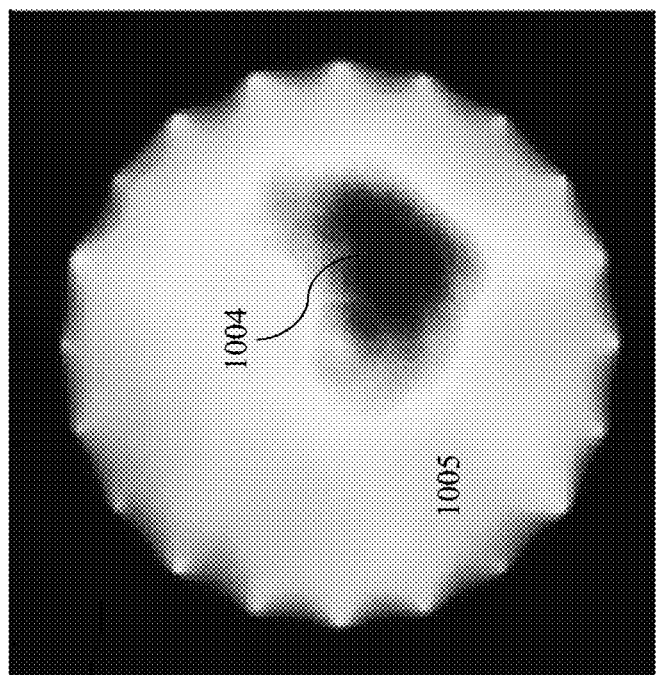
FIG. 10B illustrates a probability density function and one example of a pseudo-image of damage in a plate-like structure generated with a guided wave CT imaging array.
Figure 10B:
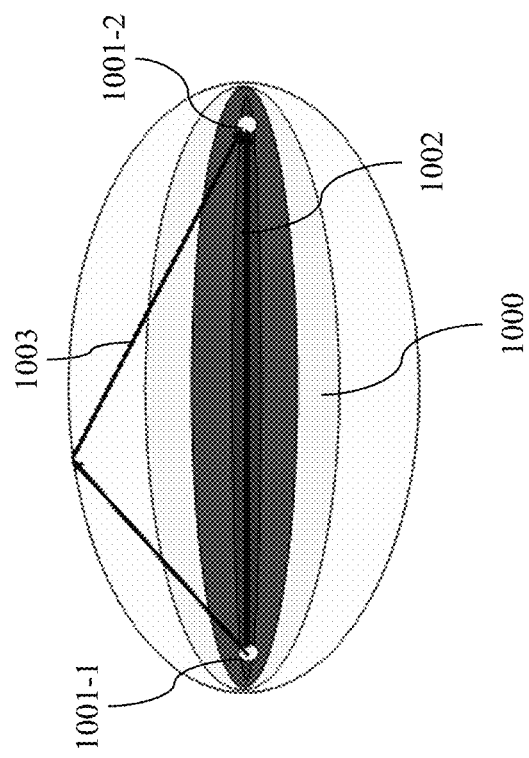

FIGS. 10A and 10B illustrate one embodiment in which at least two shear ring elements 1001 are coupled to a structure around the perimeter of an area 1005 to be monitored using guided wave CT imaging. SH wave signals are transmitted between all elements 1001 in the array. A damage probability function 1000, which accounts for both direct 1002 and indirect 1003 wave paths, is mapped onto each signal path 1006 and scaled according to at least one signal parameters to generate a pseudo-image 1007 of damage 1004 in the structure within the array perimeter. In some examples of this embodiment, baseline data is used as a reference comparison for the guided wave signals.

Figure 11A:
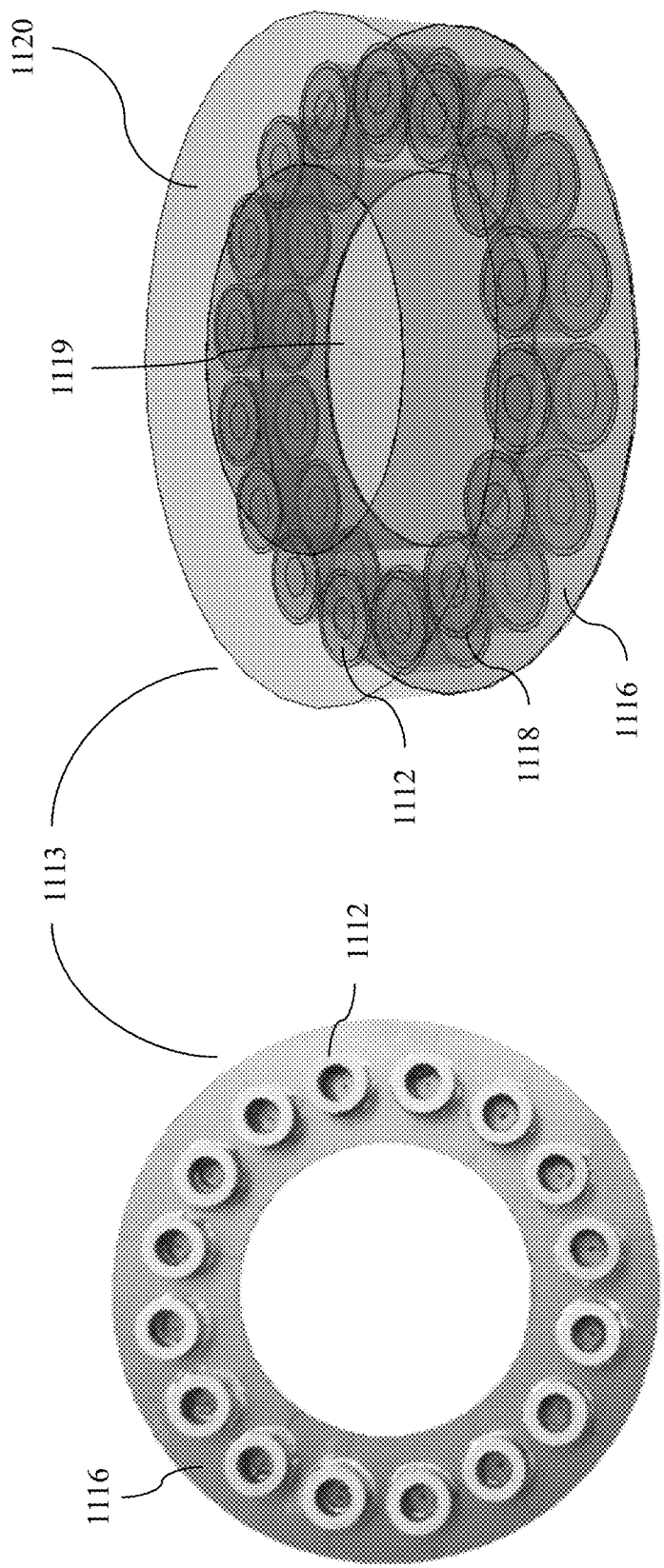
FIG. 11A illustrates a 16-element circular array of shear ring elements.
Figure 11B:
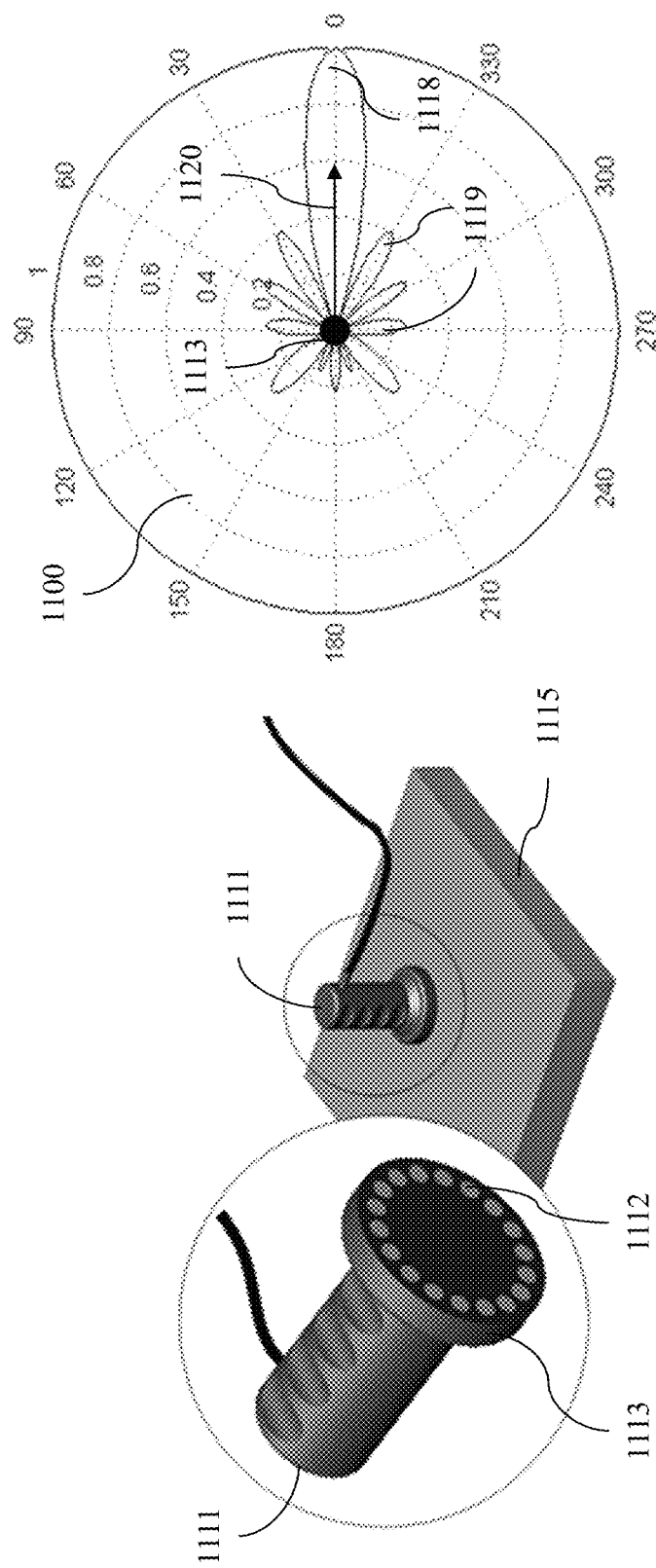
FIG. 11B illustrates the beam directivity profile of a circular guided wave beam steering phased array.

FIGS. 11A-11D illustrate one embodiment in which at least two shear ring elements 1112 are coupled to a structure 1115. Such a system is described in commonly assigned U.S. patent application Ser. No. 13/901,786, filed May 24, 2013, entitled "Systems and Methods for Damage Detection in Plate-Like Structures Using Guided Wave Phased Arrays," the entirety of which is incorporated by reference herein. At least one of time delays and amplitude factors are applied to the individual elements 1112 to generate SH guided waves in the structure that are focused to at least one point or steered in at least one direction 1120 in said structure as best seen in FIG. 11B. The focused or steered beam will have a known profile 1100, including a main lobe 1118 and sidelobes 1119, depending on the dimensions of the array 1113, the guided wave mode and frequency, and the steering direction 1120. As shown in FIG. 11C, reflections 1106 and 1107 from defects 1102 and 1103 or structural features 1104 are then detected by the at least two elements and recorded in a machine readable storage medium. The recorded guided wave data is subsequently processed to determine the presence, location, and severity of defects in the structure and generate a pseudo-image 1105 of the structure. Back-propagation post-processing is also applied to the collected guided wave data in some embodiments to further improve focusing and beam steering capabilities.

Using plate structures as an example and taking into account the guided wave dispersion and the wave divergence in the plate, the time signal at a point located in the far field of an array element can be approximately expressed as:

$$s'(t) = \frac{1}{\sqrt{x}} \int_{-\infty}^{\infty} S(\omega) e^{-ik(\omega)x} d\omega \qquad \text{Eq. (1)}$$

Where, $S(\omega)$ is the Fourier transform of the time domain guided wave input signal;

x is the distance away from the array element; and k represents the wave number.

The wave number k is a function of circular frequency ω for guided wave modes with dispersion. For the pulse-echo mode, the reflected guided wave signal introduced by a defect located in the far field of the array can then be approximately written as:

$$G_n(t) = \frac{\gamma \delta}{r_d} \int_{-\infty}^{\infty} S(\omega) e^{-ik(\omega)2r_d} e^{ik(\omega)d_n} d\omega \qquad \text{Eq. (2)}$$

Where,
where δ is the signal magnification coefficient introduced by the constructive interference of the signals generated by all of the phased elements;
γ is the reflection coefficient;
$r_d$ is the distance from the defect to the center of the array;
the subscript n represents that the reflection is received by the nth array element; and
d denotes the propagation distance that needs to be compensated for beam steering to the angle where the defect locates.

The wave number domain signal synthesis of the signals described by Equation (2) can be conducted using the following equation:

$$\sum_n B_n G_n(t) = \frac{\gamma \delta N}{r_d} \int_{-\infty}^{\infty} S(\omega) e^{-ik(\omega)2r_d} d\omega \qquad \text{Eq. (3)}$$

Where,
N is the number of array elements, and
$B_n$ is the back-propagation term:

$$B_n = e^{-ik(\omega)d_n} \qquad \text{Eq. (4)}$$

As shown in Equation (4), the dispersion relation of the guided wave modes is included in the back-propagation process so that the dispersion effects that could decrease defect detection resolution can be removed from the wave number domain synthesized signals. In some embodiments, Equation (3) can be implemented using Fast Fourier Transforms ("FFT"). The wave number domain signal synthesis is therefore also fast.

An advanced deconvolution method can be combined with the real-time guided wave phased array and the wave number domain signal synthesis as well to suppress image artifacts caused by the side lobes of the phased array as disclosed in the Ph.D. thesis, "Ultrasonic Guided Wave Phased Array for Isotropic and Anisotropic Plates," by F. Yan, the entirety of which is herein incorporated by reference.

Apodization may be applied during data collection and post-processing to reduce the sidelobes in the image. In one example of this embodiment, the guided wave excitation and recording is achieved with a multi-channel pulser-receiver system 1114 with programmable time delay and amplitude factors. In another example of this embodiment, the guided wave excitation and recording is achieved with a single-channel pulser-receiver system and a multiplexer.

In some embodiments, at least two shear ring elements 1112 are coupled to a structure 1115, and each of the at least two elements is pulsed sequentially to generate SH guided waves in the structure in all direction while each of the remaining elements is used to detect the reflections from defects or structural features, which are recorded in a machine readable medium. Such configurations are described in commonly assigned U.S. patent application Ser. No. 14/466,657, filed Aug. 22, 2014, entitled "Ultrasonic Guided Wave Corrosion Detection and Monitoring System and Method for Storage Tank Floors and Other Large-Scale, Complex, Plate-Like Structures," the entirety of which is incorporated by reference herein. The recorded guided wave data is subsequently processed to determine the presence, location, and severity of defects in the structure and generate a pseudo-image 1105 of the structure using a back-propagation post-processing algorithm. In one example of this embodiment, the guided wave excitation and recording is achieved with a multi-channel pulser-receiver system 1114. In another example of this embodiment, the guided wave excitation and recording is achieved with a single-channel pulser-receiver system and a multiplexer.

In some embodiments, the pseudo-image of the structure is compared to preciously-generated pseudo-images of the structure to perform structural health monitoring. Additional post-processing algorithms including static feature suppression may also be applied during the SHM process.

Figure 11D:
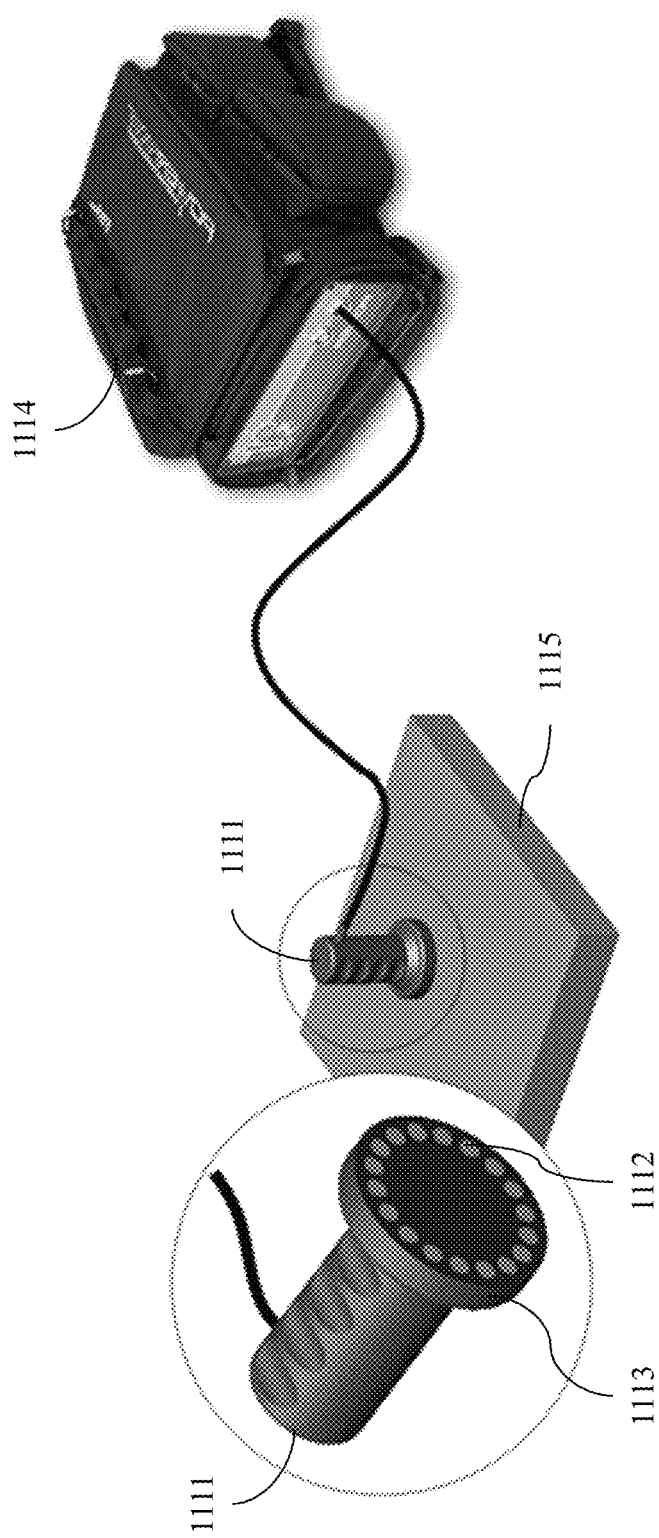
FIG. 11D illustrates one embodiment of a guided wave phased array system.

In some embodiments, such as shown in FIGS. 11A and 11D, the at least two shear ring elements 1112 are packaged into a housing 1111, comprising a faceplate 1116, isolating material 1118 around each element, an isolating core 1119, and a back fill material 1120.

Figure 12A:
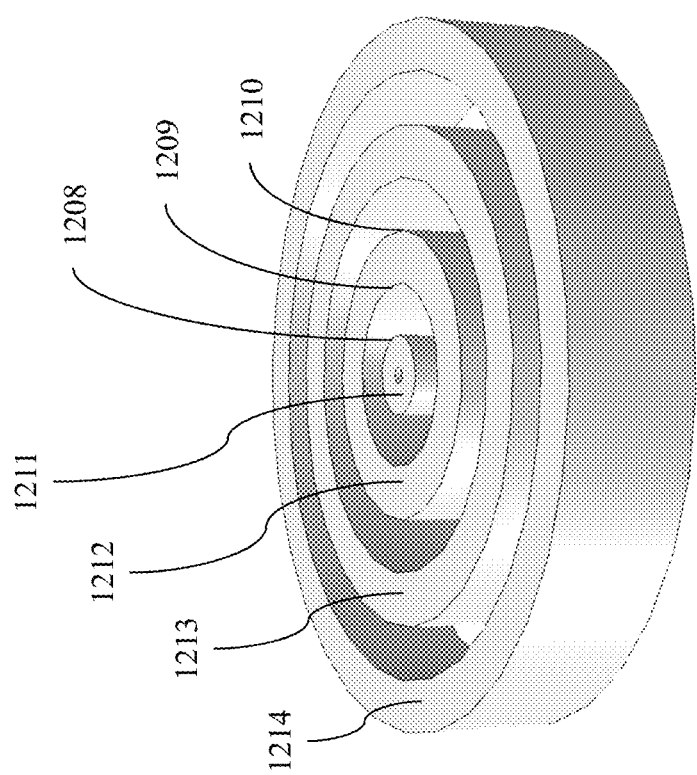
FIG. 12A illustrates a 4-element shear ring annular array.
Figure 12B:
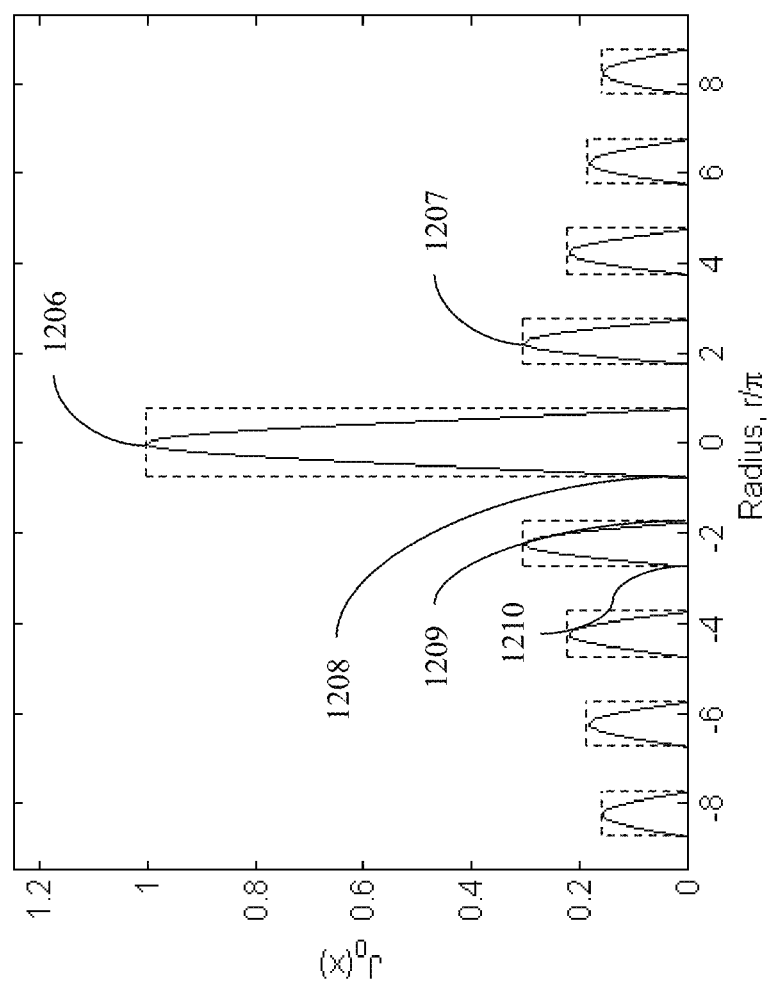
FIG. 12B illustrates a zero-order Bessel function and its relation to the geometry of one embodiment of a shear ring annular array.
Figure 12C:
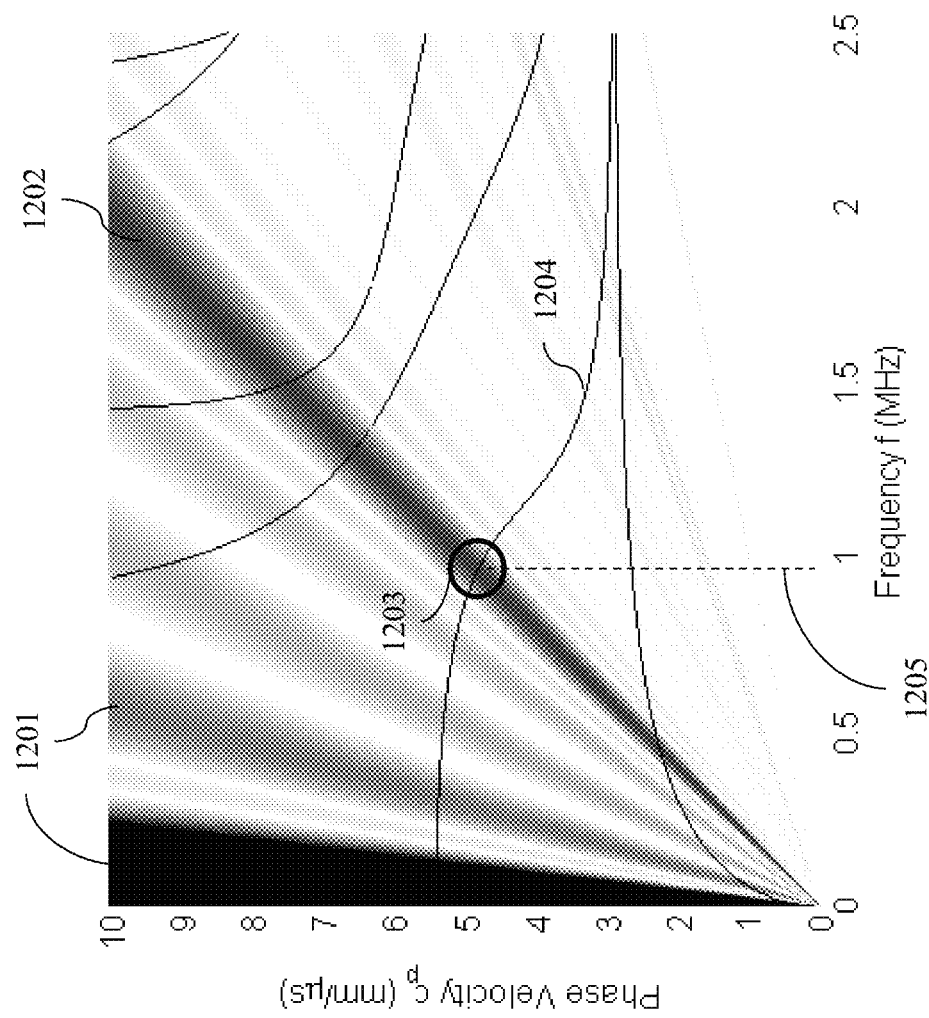
FIG. 12C illustrates one example of an excitation spectrum of an annular array superimposed over a guided dispersion curve.
Figure 12D:
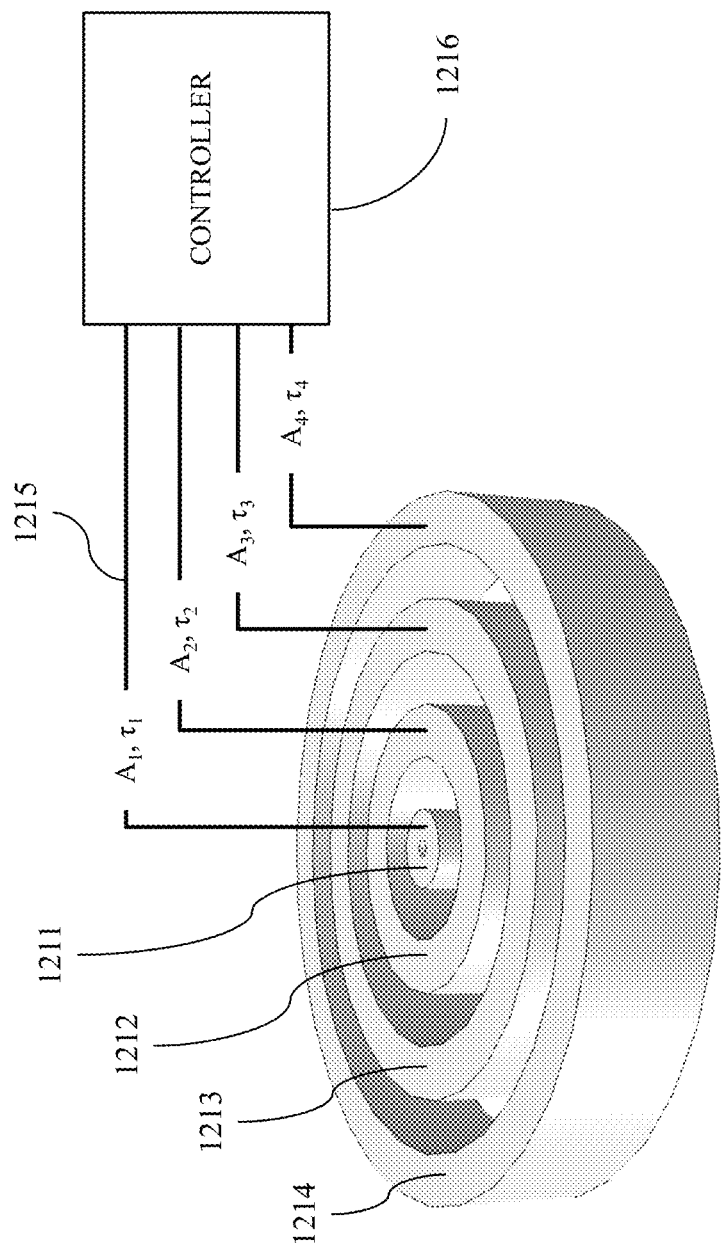
FIG. 12D illustrates a phased shear ring annular array with amplitude factors and time delays applied to the individual elements via a controller for the purpose of altering the excitation spectrum of the array.

In some embodiments of the system, such as the example illustrated in FIGS. 12A and 12D, at least two shear ring elements 1211-1214 are coupled to a structure in a concentric configuration to form an annular array transducer that is capable of preferential guided wave mode selection based on the spacing and width of the elements. In one example of this embodiment, the inner and outer diameters 1208-1210 of the shear ring elements are designed to match with the zeros an of the zero-order Bessel function shown in FIG. 12B divided by the wavenumber $k_0$ of the guided wave mode and frequency that it is intended to at least one of optimally excite and optimally detect. Additionally, in this embodiment, the relative amplitudes 1206 and 1207 of the voltage signals applied to each annular element 1211-1214 are equivalent to the amplitudes of the subsequent peaks $A_m$ of said Bessel function. The excitation spectrum $F^{ann}$ of said Bessel annular array transducer, one example of which is shown in FIG. 12C, would be described by the following equation:

$$F^{ann}(k) = \frac{1}{k} \sum_{n=1}^{2N-1} (-1)^{n-1} A_m \frac{\alpha_n}{k_0} \cdot J_1\left[\frac{\alpha_n}{k_0} k\right] \qquad \text{Eq. (5)}$$

Where,
k is wavenumber,
N is the total number of annular array elements,
$k_0$ is the target wave number,
$A_m$ is the amplitude of each subsequent Bessel function peak,
$\alpha_n$ is the nth zero of the Bessel function $J_0(x)$, and
$J_1(x)$ is the first-order Bessel function.

In FIG. 12C, the excitation spectrum of an annular array is superimposed on the guided wave dispersion curves for a particular structure. The bands of darker coloring indicate greater excitation and sensitivity to those regions of the dispersion curve. For example, mode 1204 at frequency 1205 would be strongly excited by this annular array since this point on the dispersion curve crosses the primary excitation band 1202. Additional excitation bands 1201 also exist.

In some embodiments of the system, relative amplitudes and phase delays 1215 are applied to the voltage signals sent by the controller 1216 to the at least two shear ring elements 1211-1214 that are coupled to a structure in a concentric configuration to form an annular array transducer that is capable of preferential guided wave mode selection based on the spacing and width of the elements. In this embodiment, the purpose of the amplitude factors and time delays is to alter the excitation spectrum and the corresponding excitation bands 1201 and 1202 of the annular array. In some examples, the annular array is packaged in a housing.

Figure 13:
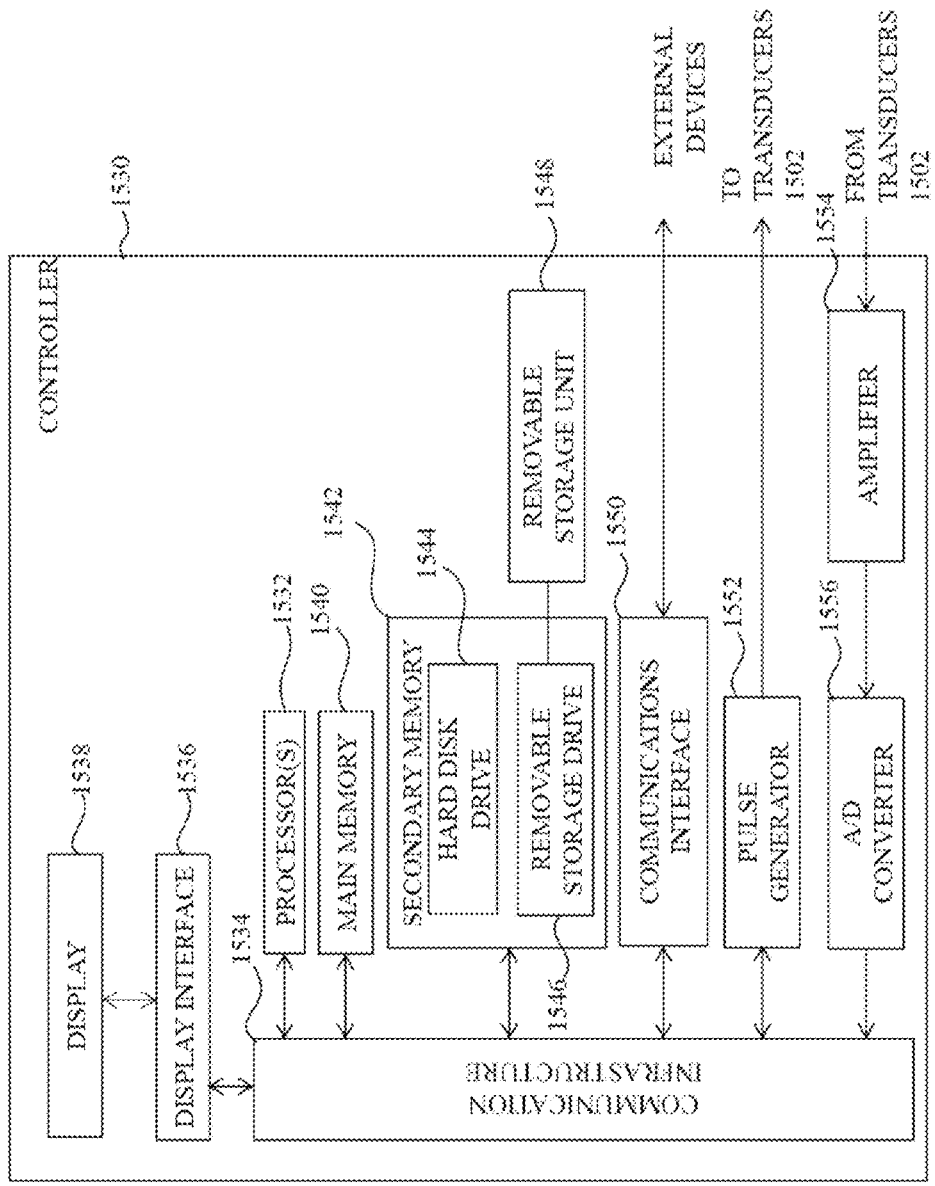
FIG. 13 illustrates one example of a block diagram of a controller of the non-destructive inspection system in accordance with some embodiments.

Referring now to FIG. 13, one example of a block diagram of a controller 1530 is shown. The controller 1530 is configured to be coupled to the plurality of transducers 1502. The controller 1530 includes one or more processors, such as processor(s) 1532. Processor(s) 1532 may be any central processing unit ("CPU"), microprocessor, microcontroller, or computational device or circuit for executing instructions and be connected to a communication infrastructure 1534 (e.g., a communications bus, cross-over bar, or network). Various software embodiments are described in terms of this exemplary controller 1530. After reading this description, it will be apparent to one of ordinary skill in the art how to implement the method using other computer systems or architectures.

In some embodiments, controller 1530 includes a display interface 1536 that forwards graphics, text, and other data from the communication infrastructure 1534 (or from a frame buffer not shown) for display on a monitor or display unit 1538 that is integrated with or separate from controller 1530.

Controller 1530 also includes a main memory 1540, such as a random access memory ("RAM"), and a secondary memory 1542. In some embodiments, secondary memory 1542 includes a persistent memory such as, for example, a hard disk drive 1544 and/or removable storage drive 1546, representing an optical disk drive such as, for example, a DVD drive, a Blu-ray disc drive, or the like. In some embodiments, removable storage drive may be an interface for reading data from and writing data to a removable storage unit 1548. Removable storage drive 1546 reads from and/or writes to a removable storage unit 1548 in a manner that is understood by one of ordinary skill in the art. Removable storage unit 1548 represents an optical disc, a removable memory chip (such as an erasable programmable read only memory ("EPROM"), Flash memory, or the like), or a programmable read only memory ("PROM")) and associated socket, which may be read by and written to by removable storage drive 1546. As will be understood by one of ordinary skill in the art, the removable storage unit 1548 may include a non-transient machine readable storage medium having stored therein computer software and/or data.

Controller 1530 may also include one or more communication interface(s) 1550, which allows software and data to be transferred between controller 1530 and external devices such as, for example, transducers 1502 and optionally to a mainframe, a server, or other device. Examples of the one or more communication interface(s) 1550 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 1550 are in the form of signals, which may be electronic, electromagnetic, optical, or other signals capable of being received by communications interface 1550. These signals are provided to communications interface(s) 1550 via a communications path or channel. The channel may be implemented using wire or cable, fiber optics, a telephone line, a cellular link, a radio frequency ("RF") link, or other communication channels.

In this document, the terms "computer program medium" and "non-transient machine readable medium" refer to media such as removable storage units 1548 or a hard disk installed in hard disk drive 1544. These computer program products provide software to controller 1530. Computer programs (also referred to as "computer control logic") may be stored in main memory 1540 and/or secondary memory 1542. Computer programs may also be received via communications interface(s) 1550. Such computer programs, when executed by a processor(s) 1532, enable the controller 1530 to perform the features of the method discussed herein.

In an embodiment where the method is implemented using software, the software may be stored in a computer program product and loaded into controller 1530 using removable storage drive 1546, hard drive 1544, or communications interface(s) 1550. The software, when executed by a processor(s) 1532, causes the processor(s) 1532 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Controller 1530 also includes a pulse generator 1552 configured to output a variety of pulses to transducers 1502. For example, pulse generator 1552 may transmit time-delayed control signals to transducers 1502 and/or pulse generator 1552 may transmit control signals of varying amplitudes to transducers 1502.

An amplifier 1554 is configured to amplify signals received from transducers 1502. Such signals received by transducers 1502 include reflections of waves from structural features and other anomalies, e.g., corrosion in a plate or plate-like structures, in response to signals transmitted by pulse generator 1552. An analog to digital ("A/D") converter 1556 is coupled to an output of amplifier 1554 and is configured to convert analog signals received from amplifier 1554 to digital signals. The digital signals output from A/D converter 1556 may be transmitted along communication infrastructure 1534 where they may undergo further signal processing by processor(s) 1532 as will be understood by one of ordinary skill in the art.

In some embodiments, the disclosed methods can be embodied at least partially be embodied in the form of program code embodied in tangible media, such as floppy diskettes, CD-ROMs, DVD-ROMs, Blu-ray disks, hard drives, solid-state drives, Flash memory drives, or any other machine-readable storage medium, wherein, when the program code is loaded into and executed by a machine, such as a computer, the machine becomes an apparatus for practicing the method. The disclosed methods also can be at least partially embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the method. When implemented on a general-purpose processor, the program code segments combine with the processor to provide a unique device that operates analogously to specific logic circuits.

Although the systems and methods have been described in terms of exemplary embodiments, they are not limited thereto. Rather, the appended claims should be construed broadly, to include other variants and embodiments of the disclosed systems and methods, which may be made by those skilled in the art without departing from the scope and range of equivalents of the systems and methods.

The invention claimed is:

1. An ultrasonic guided wave system, comprising:
   at least one first circumferentially-polarized piezoelectric $d_{15}$ shear ring element configured to be coupled to a structure; and
   a controller electrically coupled to the at least one first circumferentially-polarized piezoelectric $d_{15}$ shear ring element, the controller including
      a machine readable storage medium, and
      a processor in signal communication with the machine readable storage medium, the processor configured to
         cause a pulse generator to pulse the at least one first circumferentially-polarized piezoelectric $d_{15}$ shear ring element such that shear horizontal-type guided wave energy is transmitted omnidirectionally in the structure,
         process at least one received guided wave signal to identify a presence and location of at least one possible defect in the structure, and
         store the at least one guided wave signal and defect detection data in the machine readable storage medium.

2. The system of claim 1, wherein the at least one first circumferentially-polarized piezoelectric $d_{15}$ shear ring element is configured to receive the at least one received guided wave signal.

3. The system of claim 1, wherein at least one second circumferentially-polarized piezoelectric $d_{15}$ shear ring element is electrically coupled to the controller and is configured to receive the at least one received guided wave signal.

4. The system of claim 3, wherein the at least one second circumferentially-polarized piezoelectric $d_{15}$ shear ring element is configured to receive guided wave signals propagating in the structure.

5. The system of claim 1, wherein the at least one first circumferentially-polarized piezoelectric $d_{15}$ shear ring element is disposed in a housing.

6. The system of claim 1, wherein the at least one first circumferentially-polarized piezoelectric $d_{15}$ shear ring element includes a plurality of circumferentially-polarized piezoelectric $d_{15}$ shear ring elements configured to be disposed around a perimeter of an area of the structure, and wherein the processor is configured to
   generate a plurality of guided wave signals using a first set of the plurality of circumferentially-polarized piezoelectric $d_{15}$ shear ring elements;
   generate tomographic pseudo-image of structural changes of the structure based on a plurality of guided wave signals received from the structure at a second set of the plurality of circumferentially-polarized piezoelectric $d_{15}$ shear ring elements coupled to the structure.

7. The system of claim 1, wherein the at least one first circumferentially-polarized piezoelectric $d_{15}$ shear ring element includes a plurality of circumferentially-polarized piezoelectric $d_{15}$ shear ring elements configured to be coupled to the structure, and wherein the processor is configured to
   cause the pulse generator to pulse a first set of the plurality of circumferentially-polarized piezoelectric $d_{15}$ shear ring elements using at least one of an active time delay and amplitude factors such that a plurality of guided waves are transmitted in the structure,
   apply a back-propagation algorithm to guided wave signals received from the structure by a second set of the plurality of circumferentially-polarized piezoelectric $d_{15}$ shear ring elements, and
   generate a first pseudo-image identifying a location and a severity of defects in the structure.

8. The system of claim 7, wherein the processor is configured to compare the first pseudo-image to a second previously generated pseudo-image to carry out structural health monitoring.

9. The system of claim 7, wherein the first set of the plurality of circumferentially-polarized piezoelectric $d_{15}$ shear ring elements is different from the second set of the plurality of circumferentially-polarized piezoelectric $d_{15}$ shear ring elements.

10. The system of claim 7, wherein the first set of the plurality of circumferentially-polarized piezoelectric $d_{15}$ shear ring elements is the same as the second set of the plurality of circumferentially-polarized piezoelectric $d_{15}$ shear ring elements.

11. The system of claim 7, wherein at least one first circumferentially-polarized piezoelectric $d_{15}$ shear ring element is included in the first set of the plurality of circumferentially-polarized piezoelectric $d_{15}$ shear ring elements and in the second set of the plurality of circumferentially-polarized piezoelectric $d_{15}$ shear ring elements.

12. The system of claim 1, wherein the at least one first circumferentially-polarized piezoelectric $d_{15}$ shear ring element includes a plurality of circumferentially-polarized piezoelectric $d_{15}$ shear ring elements configured to be coupled to the structure, and wherein the processor is configured to:
   cause the pulse generator to sequentially pulse each of a first set of the plurality circumferentially-polarized piezoelectric $d_{15}$ shear ring elements to generate a plurality of guided waves in the structure,
   apply a back-propagation algorithm to a plurality of guided wave signals received from the structure at a second set of the plurality of circumferentially-polarized piezoelectric $d_{15}$ shear ring elements, and
   generate a first pseudo-image describing a location and a severity of defects in the structure.

13. The system of claim 12, wherein the first pseudo-image is compared to a second previously generated pseudo-image to carry out structural health monitoring.

14. The system of claim 12, wherein the first set of the plurality of circumferentially-polarized piezoelectric $d_{15}$ shear ring elements is different from the second set of the plurality of circumferentially-polarized piezoelectric $d_{15}$ shear ring elements.

15. The system of claim 12, wherein the first set of the plurality of circumferentially-polarized piezoelectric $d_{15}$ shear ring elements is the same as the second set of the plurality of circumferentially-polarized piezoelectric $d_{15}$ shear ring elements.

16. The system of claim 12, wherein at least one first circumferentially-polarized piezoelectric $d_{15}$ shear ring element is included in the first set of the plurality of circumferentially-polarized piezoelectric $d_{15}$ shear ring elements and in the second set of the plurality of circumferentially-polarized piezoelectric $d_{15}$ shear ring elements.

17. The system of claim 1, wherein the at least one first circumferentially-polarized piezoelectric $d_{15}$ shear ring element includes a plurality of circumferentially-polarized, piezoelectric $d_{15}$ shear ring elements configured to be disposed on the structure in a concentric fashion to control a wavelength excitation spectrum of shear horizontal-type guided wave modes excited and detected in the structure.

18. The system of claim 17, wherein an inner diameter and an outer diameter of the plurality of circumferentially-polarized piezoelectric $d_{15}$ shear ring elements are designed based on a zero-order Bessel function.

* * * * *